US011944966B2

(12) United States Patent
Aksimentiev

(10) Patent No.: US 11,944,966 B2
(45) Date of Patent: Apr. 2, 2024

(54) SYSTEMS AND METHODS FOR HIGH-FIDELITY CAPTURE, THREADING, AND INFINITE-DEPTH SEQUENCING OF SINGLE NUCLEIC ACID MOLECULES

(71) Applicant: THE BOARD OF TRUSTEES OF THE UNIVERSITY OF ILLINOIS, Urbana, IL (US)

(72) Inventor: Aleksei Aksimentiev, Urbana, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 159 days.

(21) Appl. No.: 17/513,516

(22) Filed: Oct. 28, 2021

(65) Prior Publication Data
US 2022/0134337 A1    May 5, 2022

Related U.S. Application Data

(60) Provisional application No. 63/108,117, filed on Oct. 30, 2020.

(51) Int. Cl.
*B01L 3/00* (2006.01)
*C12Q 1/6869* (2018.01)

(52) U.S. Cl.
CPC ...... *B01L 3/502715* (2013.01); *C12Q 1/6869* (2013.01); *B01L 2200/0652* (2013.01);
(Continued)

(58) Field of Classification Search
CPC .......... B01L 2300/0636; B01L 3/5027; B01L 2200/0652; B01L 2300/0663;
(Continued)

(56) References Cited

U.S. PATENT DOCUMENTS

| 2010/0084276 A1* | 4/2010 | Lindsay ............. G01N 27/3276 204/403.01 |
| 2018/0088104 A1 | 3/2018 | Aksimentiev et al. |
| 2022/0326214 A1* | 10/2022 | Postma ............ G01N 33/48721 |

OTHER PUBLICATIONS

Choudhary, Adnan et al., "High-Fidelity Capture, Threading, and Infinite-Depth Sequencing of Single DNA Molecules with a Double-Nanopore System", ACS Nano 2020, 14, 15566-15576, www.acsnano.org, Nov. 11, 2020, 11 pages.
(Continued)

*Primary Examiner* — Brian J. Sines
(74) *Attorney, Agent, or Firm* — Guntin & Gust, PLC; Matthew Tropper

(57) ABSTRACT

Aspects of the subject disclosure may include, for example, an apparatus comprising: a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, and wherein the second pore extends through the membrane from the first side of the membrane to the second side of the membrane; a first channel disposed on the first side of the membrane, wherein the first channel is along a first longitudinal axis; a second channel disposed on the first side of the membrane, wherein the second channel is along a second longitudinal axis, and wherein the first channel and the second channel are disposed side by side adjacent to each other; a third channel disposed on the second side of the membrane, wherein the third channel is along a third longitudinal axis, wherein the third channel is in first fluid communication with the first channel via the first pore, and wherein the third channel is in second fluid communication with the second channel via the second pore; and one or more sensors disposed at one or more locations to facilitate sequencing of
(Continued)

a molecule that extends from the first channel, through the first pore across at least a portion of the third channel, and through the second pore into the second channel. Additional embodiments are disclosed.

22 Claims, 24 Drawing Sheets

(52) U.S. Cl.
CPC ............... *B01L 2300/0663* (2013.01); *B01L 2300/0896* (2013.01); *B01L 2400/0415* (2013.01)

(58) Field of Classification Search
CPC ..... B01L 2300/0896; B01L 2400/0415; G01N 15/02; C12Q 1/6869
See application file for complete search history.

(56) References Cited

OTHER PUBLICATIONS

Choudhary, Adnan et al., "Supporting Information for: High-Fidelity Capture, Threading and Infinite-Depth Sequencing of Single DNA Molecules with a Double-Nanopore System", ACS Nano 2020, 14, www.acsnano.org, Nov. 11, 2020, 9 pages.
Aksimentiev, Aleksij et al., "Microscopic Kinetics of DNA Translocation through Synthetic Nanopores", Biophysical Journal, vol. 87, Sep. 2004.
Belkin, Maxim et al., "Plasmonic Nanospores for Trapping, Controlling Displacement, and Sequencing of DNA", ACSNano, vol. 9, No. 11, Sep. 24, 2015, 14 pages.
Comer, Jeffrey et al., "Predicting the DNA Sequence Dependence of Nanopore Ion Current Using Atomic-Resolution Brownian Dynamics", The Journal of Physical Chemistry, 116, 2012, 18 pages.
Hemmig, Elisa A. et al., "Optical Voltage Sensing Using DNA Origami", Nano Lett. 2018, 18, Feb. 12, 2018, 10 pages.
Heng, et al., "Sizing DNA Using a Nanometer-Diameter Pore", Biophysical Journal, vol. 87, Oct. 2004, 7 pages.
Liu, Xu et al., "Controlling DNA Tug-of-War in a Dual Nanopore Device", Small, www.small-journal.com, Published online on Jun. 13, 2019, 13 pages.
Liu, Xu et al., "Flossing DNA in a Dual Nanopore Device", Small 2020, 16, Advanced Science News (www.advancedsciencenews.com); Nano-Micro Small (www.small-journal.com), Published online on Dec. 20, 2019, 11 pages.
Luan, Binquan et al., "Electro-osmotic screening of the DNA charge in a nanopore", Physical Review E 78, 021912, Aug. 26, 2008, 4 pages.
Maffeo, Christopher et al., "A Coarse-Grained Model of Unstructured Single-Stranded DNA Derived From Atomistic Simulation and Single-Molecule Experiment", Journal of Chemical Theory and Computation, Jun. 3, 2014, pp. 2891-2896.
Maffeo, Christopher et al., "MrDNA: a multi-resolution model for predicting the structure and dynamics of DNA systems", Nucleic Acids Research, vol. 48, No. 9, Mar. 31, 2020, 12 pages.
Phillips, James C. et al., "Scalable molecular dynamics on CPU and GPU architectures with NAMD", J. Chem. Phys. 153, 044130, Jul. 30, 2020, 34 pages.
Pud, Sergii et al., "Mechanical Trapping of DNA in a Double-Nanopore System", DOI: 10.1021/acs.nanolett.6b04642 Nano Lett. 2016, 16, pp. 8021-8028 (including a Supporting Information document) Nov. 28, 2016, 34 pages.
Shankla, Manish et al., "Conformational transitions and stop-and-go nanopore transport of single-stranded DNA on charged graphene", Nature Communications, Oct. 9, 2014, 9 pages.
Tian, Kai et al., "Interference-Free Detection of Genetic Biomarkers Using Synthetic Dipole-Facilitated Nanopore Dielectrophoresis", ACS Nano 2017, 11, Dec. 30, 2016, 10 pages.
Timp, Winston et al., "DNA Base-Calling from a Nanopore Using a Viterbi Algorithm", Biophysical Journal, vol. 102, May 2012, 3 pages.
Wells, David B. et al., "Assessing Graphene Nanopores for Sequencing DNA", Nano Letters, vol. 12, pp. 4117-4123, 2012, Jul. 10, 2012, 7 pages.
Wilson, James et al., "Rapid and Accurate Determination of Nanopore Ionic Current Using a Steric Exclusion Model", ACS Sens. 4, Mar. 1, 2019, 11 pages.
Zhang, Yuning et al., "Single Molecule DNA Resensing Using a Two-Pore Device", Small, 14, 2018, 12 pages.

\* cited by examiner

SYSTEMS AND METHODS FOR HIGH-FIDELITY CAPTURE, THREADING, AND INFINITE-DEPTH SEQUENCING OF SINGLE NUCLEIC ACID MOLECULES

CROSS REFERENCE TO RELATED APPLICATION(S)

This application claims the benefit of priority to U.S. Provisional Application No. 63/108,117, filed Oct. 30, 2020. All sections of the aforementioned application(s) and/or patent(s) are incorporated herein by reference in their entirety (including each Appendix thereof).

STATEMENT AS TO FEDERALLY SPONSORED RESEARCH

This invention was made with government support under DMR-1827346 awarded by the National Science Foundation and under P41-GM104601 awarded by the National Institutes of Health. The government has certain rights in this invention.

FIELD OF THE DISCLOSURE

The subject disclosure relates generally to systems and methods for high-fidelity capture, threading, and infinite-depth sequencing of single nucleic acid molecules, and more specifically to systems and methods utilizing a double-nanopore apparatus.

BACKGROUND

Nanopore sequencing of nucleic acids has a history of innovations that eventually made commercial nanopore sequencing possible. Nevertheless, the conventional nanopore sequencing technology typically leaves much room for improvement, especially with respect to accuracy of raw reads and detection of nucleotide modifications.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Reference will now be made to the accompanying drawings, which are not necessarily drawn to scale, and wherein.

DETAILED DESCRIPTION

As described herein, various embodiments provide for double-nanopore sequencing—an approach where a molecule (e.g., a DNA molecule) is pulled back and forth by a tug-of-war of two nanopores. Such double-nanopore sequencing according to various embodiments can potentially improve single molecule read accuracy and modification detection by offering multiple reads of the same DNA fragment. Various embodiments provide a mechanism to facilitate threading a single nucleic acid (NA) strand (such as single-stranded DNA) through both nanopores.

As described herein, various embodiments provide for single molecule DNA, RNA and/or protein sequencing; detection of epigenetic modifications; detection of posttranslational modifications; and/or detection of DNA/RNA damage.

As described herein, various embodiments provide for a double-nanopore sequencing approach that enables 100%

(or near 100%) fidelity threading and loading of individual DNA molecules and shows how such double-nanopore sequencing can be used for nanopore sequencing of homopolymer. As described herein, various embodiments provide for sequencing via repeat exposure of NA fragments.

Figure 1A:
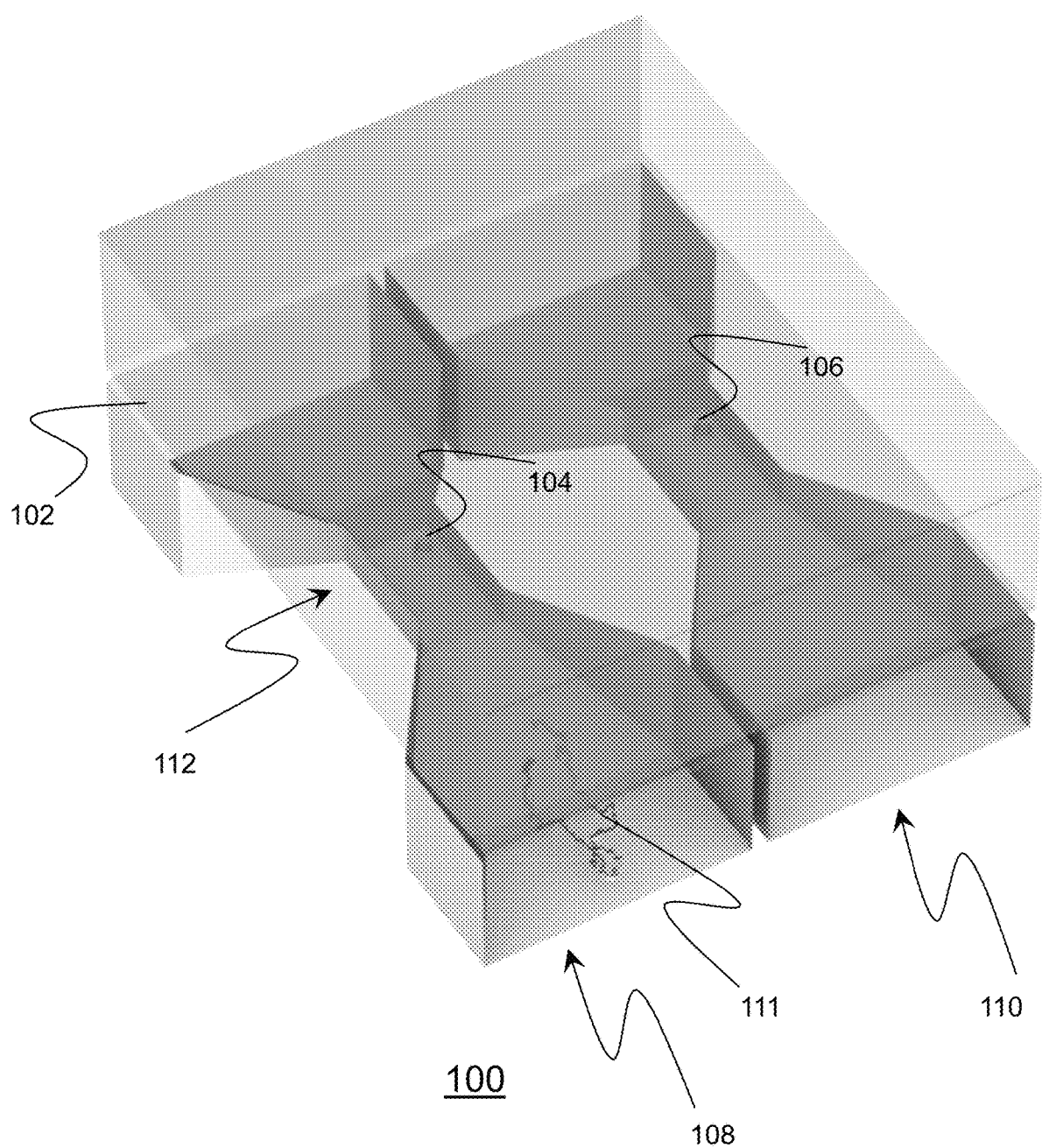
FIGS. 1A-1C depict an illustrative embodiment of an apparatus 100 for capture, threading, and sequencing of molecules (e.g., nucleic acid molecules)
Figure 1B:
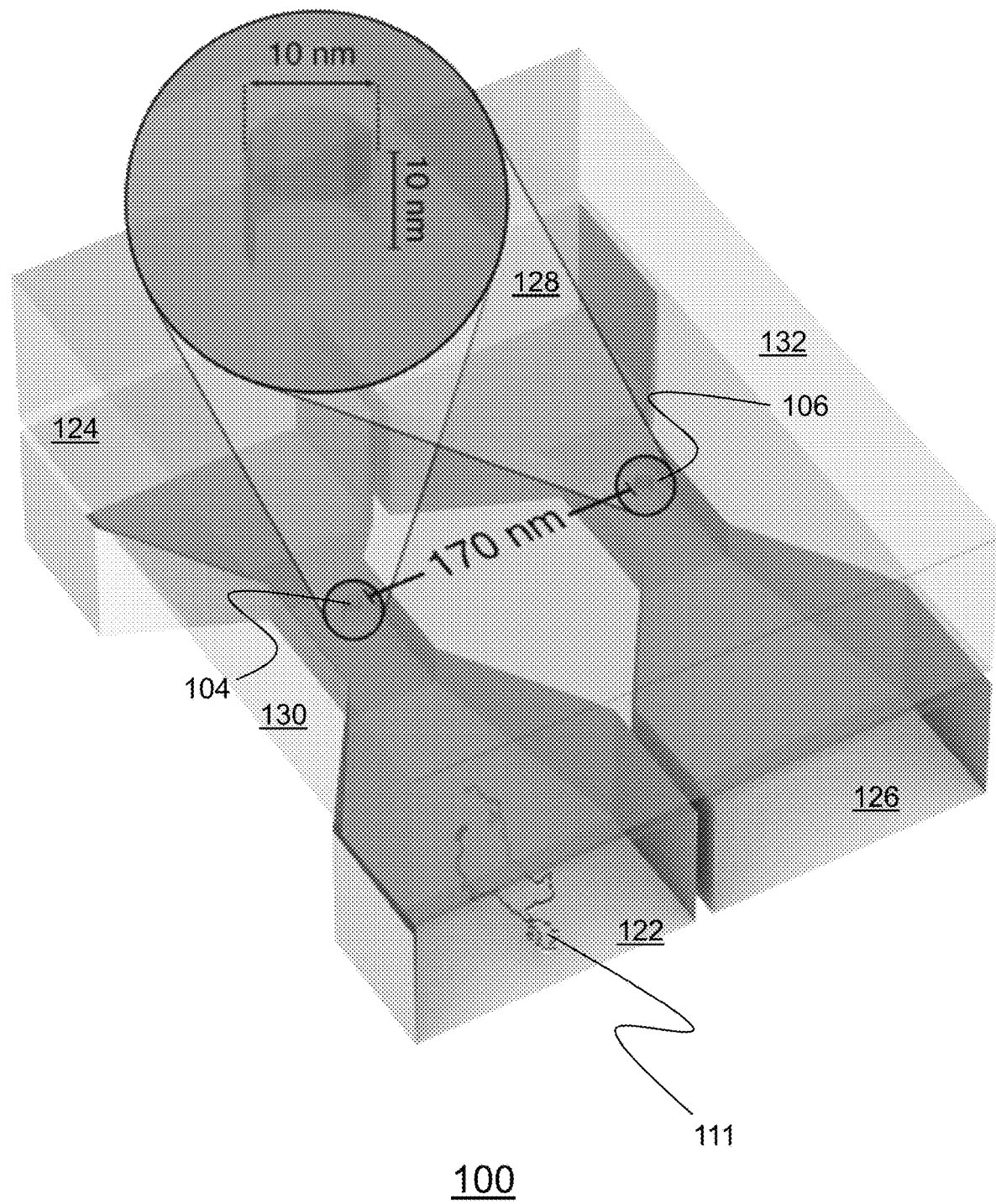
Figure 1C:
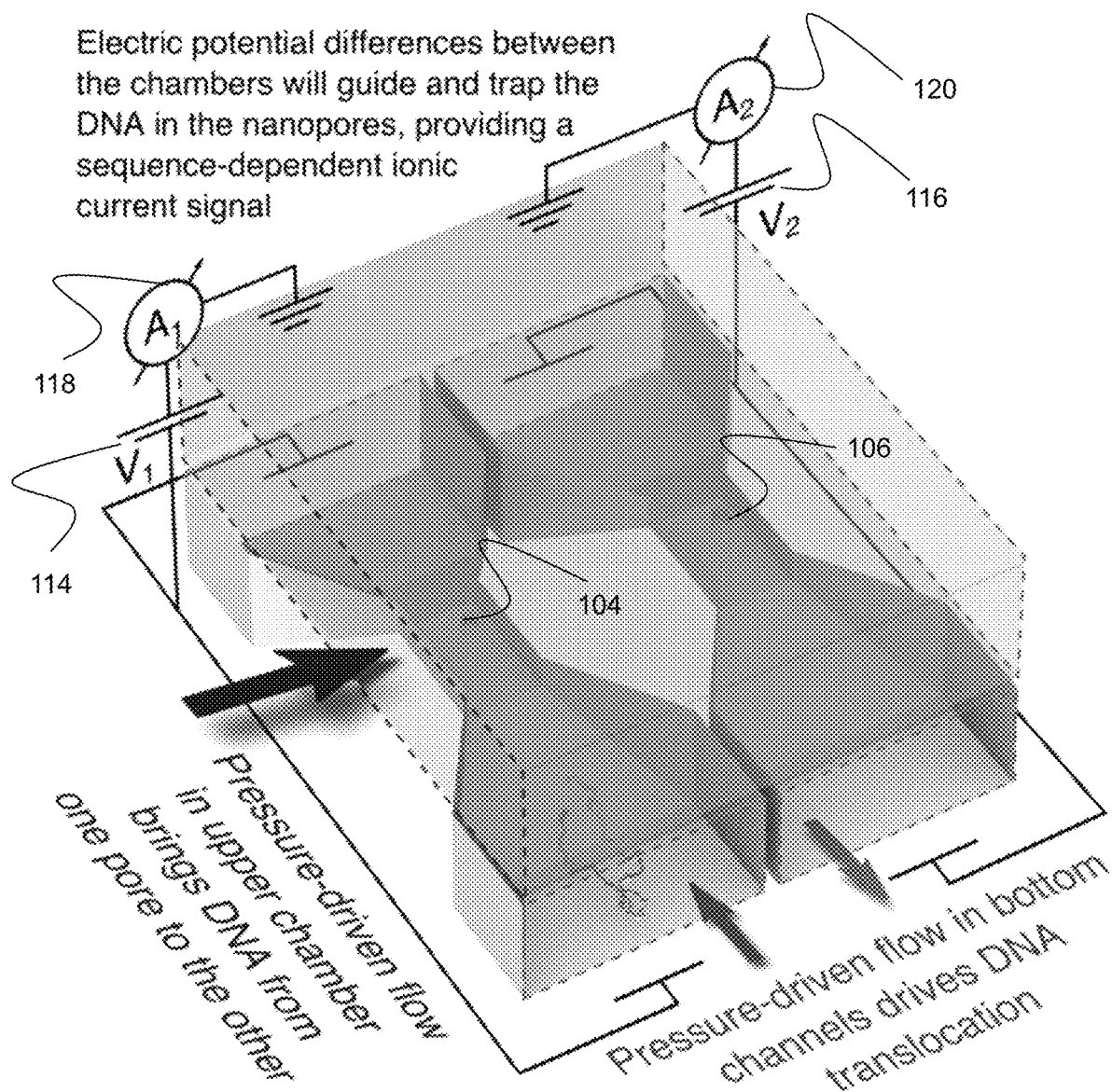
Figure 1D:
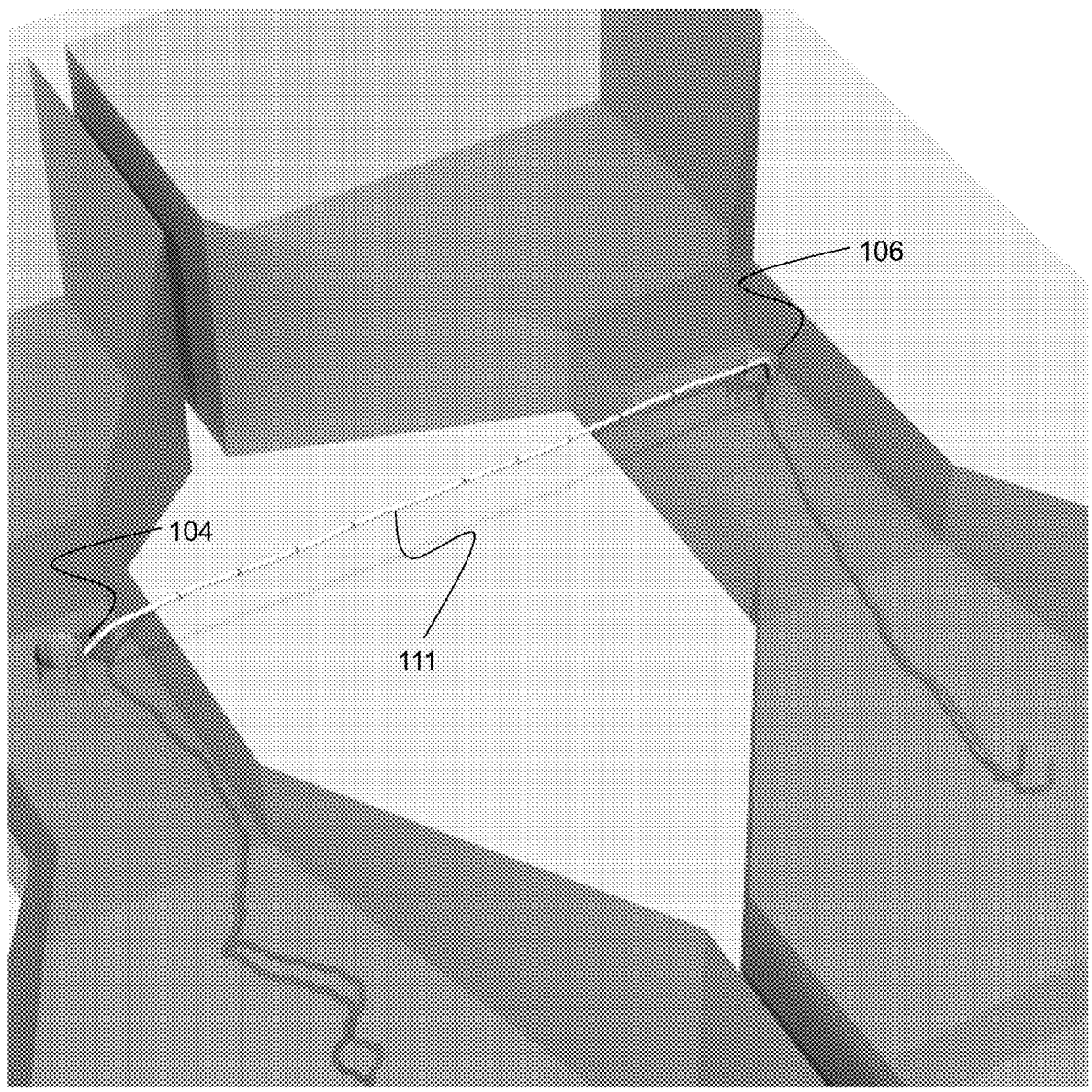
FIG. 1D depicts certain details (according to an embodiment) of the apparatus 100.

In one embodiment, an apparatus comprises: a membrane (see, e.g., 102 of FIG. 1A), wherein the membrane has a first side and a second side, wherein the membrane has a first pore (see, e.g., 104 of FIG. 1A) disposed therein, wherein the first pore extends through the membrane from the first side of the membrane to the second side of the membrane, wherein the membrane has a second pore (see, e.g., 106 of FIG. 1A) disposed therein, and wherein the second pore extends through the membrane from the first side of the membrane to the second side of the membrane; a first channel (see, e.g., the left channel 108 of FIG. 1A) disposed on the first side of the membrane, wherein the first channel is along a first longitudinal axis; a second channel (see, e.g., the right channel 110 of FIG. 1A) disposed on the first side of the membrane, wherein the second channel is along a second longitudinal axis, and wherein the first channel and the second channel are disposed side by side adjacent to each other; a third channel (see, e.g., the upper channel 112 of FIG. 1A) disposed on the second side of the membrane, wherein the third channel is along a third longitudinal axis, wherein the third channel is in first fluid communication with the first channel via the first pore, and wherein the third channel is in second fluid communication with the second channel via the second pore; and one or more sensors that are disposed at one or more locations to facilitate sequencing of a molecule (see, e.g., molecule 111 of FIG. 1D) that extends from the first channel, through the first pore across at least a portion of the third channel, and through the second pore into the second channel. In one example, the channels can be formed from materials including (but not limited to): silicon nitride, silicon oxide, graphene stack(s), boron nitride stack(s), and/or any combination thereof.

In one example, the apparatus further comprises: a first voltage source (see, e.g., $V_1$ 114 of FIG. 1C), the first voltage source being configured to apply a first voltage differential, in a first vicinity of the first pore, between the first channel and the third channel; and a second voltage source (see, e.g., $V_2$ 116 of FIG. 1C), the second voltage source being configured to apply a second voltage differential, in a second vicinity of the second pore, between the second channel and the third channel.

In another example: the first voltage differential facilitates first movement of a first end of the molecule from the first channel, through the first pore, and into the third channel; and the second voltage differential facilitates second movement of the first end of the molecule from the third channel, through the second pore, and into the second channel.

In another example, the first voltage differential is controllable independently from the second voltage differential.

In another example: the first voltage source facilitates first control of the first voltage differential independently of the second voltage differential; and the second voltage source facilitates second control of the second voltage differential independently of the first voltage differential.

In another example, the first control of the first voltage differential and the second control of the second voltage differential causes at least a portion of the molecule to be moved back and forth such that each of the one or more sensors is able to take multiple readings of the molecule.

In another example, the sequencing of the molecule comprises sequencing a portion of the molecule.

In another example, the sequencing of the molecule comprises sequencing all of the molecule.

In another example, the molecule comprises a single stranded DNA (ssDNA).

In another example, the molecule comprises a single RNA.

In another example, the molecule comprises a DNA-protein conjugate.

In another example, the apparatus further comprises at least one mechanism configured to: apply a first pressure differential between a first end (see, e.g., 122 of FIG. 1B) of the first channel and a second end (see, e.g., 124 of FIG. 1B) of the first channel; and apply a second pressure differential between a first end (see, e.g., 126 of FIG. 1B) of the second channel and a second end (see, e.g., 128 of FIG. 1B) of the second channel.

In another example: the first pressure differential facilitates movement of a first end of the molecule through the first channel, to a vicinity of the first pore; and the second pressure differential facilitates movement of the first end of the molecule through the second channel, away from a vicinity of the second pore.

In another example, the at least one mechanism comprises at least one micro-pump.

In another example: the at least one micro-pump comprises a first micro-pump and a second micro-pump; the first micro-pump applies the first pressure differential; and the second micro-pump applies the second pressure differential.

In another example: the first micro-pump facilitates first control of the first pressure differential independently of the second pressure differential; and the second micro-pump facilitates second control of the second pressure differential independently of the first pressure differential.

In another example, the first pressure differential is controllable independently from the second pressure differential.

In another example: the first longitudinal axis is substantially parallel to the second longitudinal axis; and the third longitudinal axis is substantially perpendicular to the first longitudinal axis and to the second longitudinal axis.

In another example: the first channel and the second channel are disposed below the membrane; and the third channel is disposed above the membrane.

In another example: the first channel and the second channel are disposed above the membrane; and the third channel is disposed below the membrane.

In another example: the first channel has a first end (see, e.g., 122 of FIG. 1B), a second end (see, e.g., 124 of FIG. 1B) and a first middle section (see, e.g., the narrowed cross-section between 122 and 124); the first middle section has a smaller cross-sectional area than the first end and the second end; the first middle section is located adjacent the first pore; the second channel has a third end (see, e.g., 126 of FIG. 1B), a fourth end (see, e.g., 128 of FIG. 1B), and a second middle section (see, e.g., the narrowed cross-section between 126 and 128); the second middle section has a smaller cross-sectional area than the third end and the fourth end; and the second middle section is located adjacent the second pore.

In another example, the apparatus further comprises a mechanism configured to apply a pressure differential between a first end (see, e.g., 130 of FIG. 1B) of the third channel and a second end (see, e.g., 132 of FIG. 1B) of the third channel.

In another example, the pressure differential (between 130 and 132) facilitates movement of a first end of the molecule through the third channel, from a first vicinity of the first pore to a second vicinity of the second pore.

In another example, the at least one mechanism comprises a micro-pump.

In another embodiment, an apparatus comprises: a first channel (see, e.g., the left channel 108 of FIG. 1A) disposed on a first side of a membrane (see, e.g., 102 of FIG. 1A), wherein the first channel is along a first axis; a second channel (see, e.g., the right channel 110 of FIG. 1A) disposed on the first side of the membrane, wherein the second channel is along a second axis, and wherein the first channel and the second channel are disposed adjacent to each other; a third channel (see, e.g., the upper channel 112 of FIG. 1A) disposed on a second side of the membrane, wherein the third channel is along a third axis, wherein the third channel is in first fluid communication with the first channel via a first pore (see, e.g., 104 of FIG. 1A) of the membrane, and wherein the third channel is in second fluid communication with the second channel via a second pore (see, e.g., 106 of FIG. 1A) of the membrane; a first voltage source (see, e.g., $V_1$ 114 of FIG. 1C) configured to apply a first voltage differential between the first channel and the third channel; a second voltage source (see, e.g., $V_2$ 116 of FIG. 1C) configured to apply a second voltage differential between the second channel and the third channel; a processing system including a processor; and a memory that stores executable instructions that, when executed by the processing system, facilitate performance of operations, the operations comprising: controlling the first voltage source and the second voltage source to cause back and forth movement of a molecule (see, e.g., molecule 111 of FIG. 1D) that extends from the first channel, through the first pore across at least a portion of the third channel, and through the second pore into the second channel. In various examples, one or more of the channels can be elongated (that is, long in relation to width). In various examples, one or more of the channels can have a tapered hour-glass shape.

In one example: measuring a first current flow associated with the first voltage source (see, e.g., current meter 118 of FIG. 1C) facilitates determining a type of nucleotide that is present on the molecule in a vicinity of the first pore; and measuring a second current flow associated with the second voltage source (see, e.g., current meter 120 of FIG. 1C) facilitates determining a type of nucleotide that is present on the molecule in a vicinity of the second pore.

In another example: the measuring the first current flow comprises measuring a plurality of first current flows to facilitate determining a plurality of types of nucleotides that are present on the molecule in a vicinity of the first pore as the molecule is moved back and forth through the first pore; and the measuring the second current flow comprises measuring a plurality of second current flows to facilitate determining a plurality of types of nucleotides that are present on the molecule in a vicinity of the second pore as the molecule is moved back and forth through the second pore.

In another embodiment, a non-transitory machine-readable storage medium comprises executable instructions that, when executed by a processing system including a processor, facilitate performance of operations, the operations comprising: detecting, on a first portion of a molecule (see, e.g., molecule 111 of FIG. 1D) that is moved through a first pore (see, e.g., 104 of FIG. 1D) in a membrane, a sequence of a plurality of different types of nucleotides; and detecting, on a second portion of the molecule (see, e.g., molecule 111 of FIG. 1D) that is moved through a second pore (see, e.g., 106 of FIG. 1D) in the membrane, a presence of a single particular type of nucleotide, wherein a count of adjacent occurrences of the single particular type of nucleotide on the second portion of the molecule is determined based at least in part on the sequence of the plurality of different types of nucleotides on the first portion of the molecule.

In one example: the sequence of the plurality of different types of nucleotides is detected via determination of one or more first changes of first current flow (see, e.g., current meter 118 of FIG. 1C) associated with a first voltage source (see, e.g., $V_1$ 114 of FIG. 1C) that provides a first voltage differential in a vicinity of the first pore; and the presence of the single particular type of nucleotide is detected via determination of one or more second changes of second current flow (see, e.g., current meter 120 of FIG. 1C) associated with a second voltage source (see, e.g., $V_2$ 116 of FIG. 1C) that provides a second voltage differential in a vicinity of the second pore.

Figure 18:
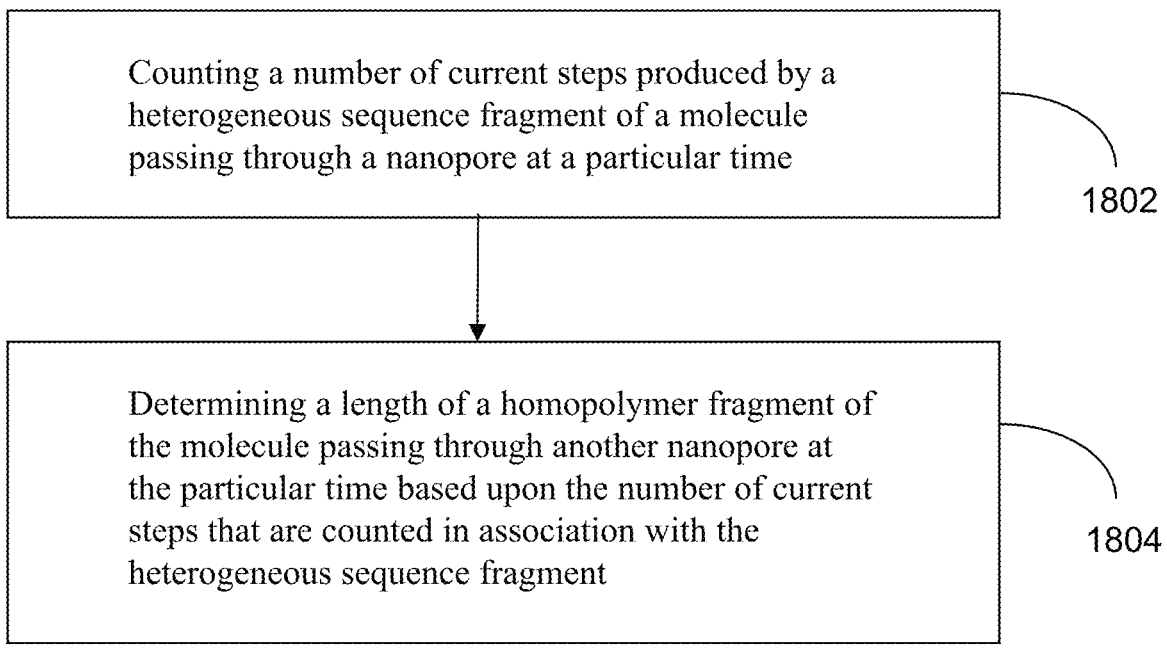
FIG. 18 depicts an illustrative method according to an embodiment.

In another embodiment (see, e.g., FIG. 18), a non-transitory machine-readable storage medium comprises executable instructions that, when executed by a processing system including a processor, facilitate performance of operations, the operations comprising: counting a number of current steps produced by a heterogeneous sequence fragment of a molecule passing through a nanopore at a particular time (see e.g., step 1802); and determining a length of a homopolymer fragment of the molecule passing through another nanopore at the particular time based upon the number of current steps that are counted in association with the heterogeneous sequence fragment (see, e.g., step 1804).

In one example, the particular time is a particular span of time.

Of note, the specific dimensions shown in the images and discussed herein are provided as examples (and are not intended to be restrictive). For example, various embodiments can provide for systems that are considerably larger (e.g., up to tens of microns). In another example, the size (e.g., diameter) of each nanopore can be in the range of 1 to 100 ns (inclusive). In another example, the distance between nanopores can be any appropriate distance in view of the length of the molecule being sequenced.

In various examples, the flows in the two adjacent channels (e.g., channels 108 and 110) can be in the same direction or different directions.

In various examples, the voltage differentials can be switched on, switched off, or adjusted (changed) to various values. In one example, a molecule being captured in a pore can act as a trigger to switch and/or adjust a voltage differential (e.g., a voltage difference between two channels). For instance, when a molecule is captured in the first pore (the capture can be detected, for example, by a change in current associated with the first pore), the capture can trigger a reduction in voltage magnitude associated with the first/third channels (the capture can also trigger a change in fluid flow in one or more channels).

In various examples, capture of a molecule in both pores can trigger turning off all fluid flows (e.g., turning off fluid flows in the first, second and third channels).

In various examples, detection of one or more homopolymers is enabled. This can be enabled, for example, by reading a sequence of a portion of a molecule using a first pore and reading (at the same time) another sequence of another portion of the molecule using a second pore.

In various examples, sequencing of a molecule (e.g., ssDNA molecule) can be done via sensing of current.

In one example, responsive to the molecule 111 being captured by both pores 104, 106, the flow in the upper channel 112 can be turned off.

In one example, responsive to the molecule 111 being captured by both pores 104, 106, the flow in the left channel 108 can be turned off and the flow in the right channel 110 can be turned off.

Figure 1E:
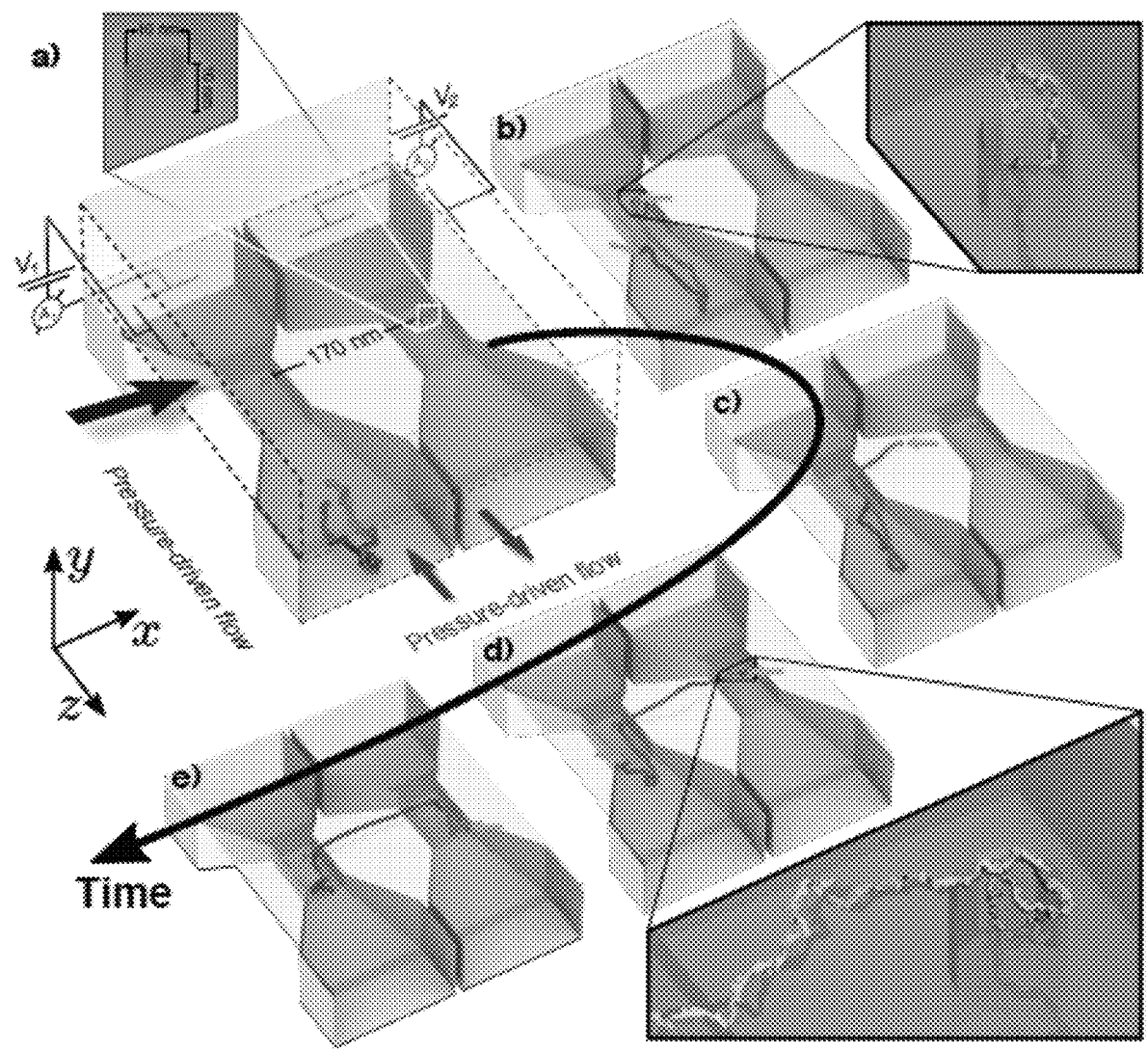
FIG. 1E depicts five views (a-e) of movement (over time) of a molecule through the apparatus 100 (according to an embodiment)

Referring now to FIG. 1E, this depicts five views (a-e) of movement (over time) of a molecule through the apparatus 100. More particularly, this figure depicts MD simulation of ssDNA threading through a double-nanopore system:
  (a) Initial configuration of the system. Two cross channels (aligned with the z axis) are connected to a common flow chamber (aligned with the x-z plane) through two nanopores (aligned with the y axis). The electric potential in each of the cross channels ($V_1$ and $V_2$) as well as the pressure difference in each channel ($\Delta p_1$, $\Delta p_2$) and the flow chamber ($\Delta p_{ch}$) can be independently controlled. The walls of the lower two delivery channels are depicted as solid surfaces; all other surfaces are semitransparent. A 1000-nucleotide ssDNA molecule is shown using a green-to-blue color gradient.
  (b) Capture of ssDNA by the first nanopore. The DNA strand was driven from the inlet of a cross channel by a pressure difference $\Delta p_1 32$ 0.05 atm; $V_1$=600 mV. Green and blue arrows mark the ends of ssDNA.
  (c) Flow-assisted delivery of ssDNA toward the second nanopore ($\Delta p_{ch}$=0.2 atm; $V_1$=−100 mV; $V_2$=+600 mV).
  (d) Capture of ssDNA by the second nanopore.
  (e) Final configuration of ssDNA. $V_1$=$V_2$=+600 mV.

Figure 1F:
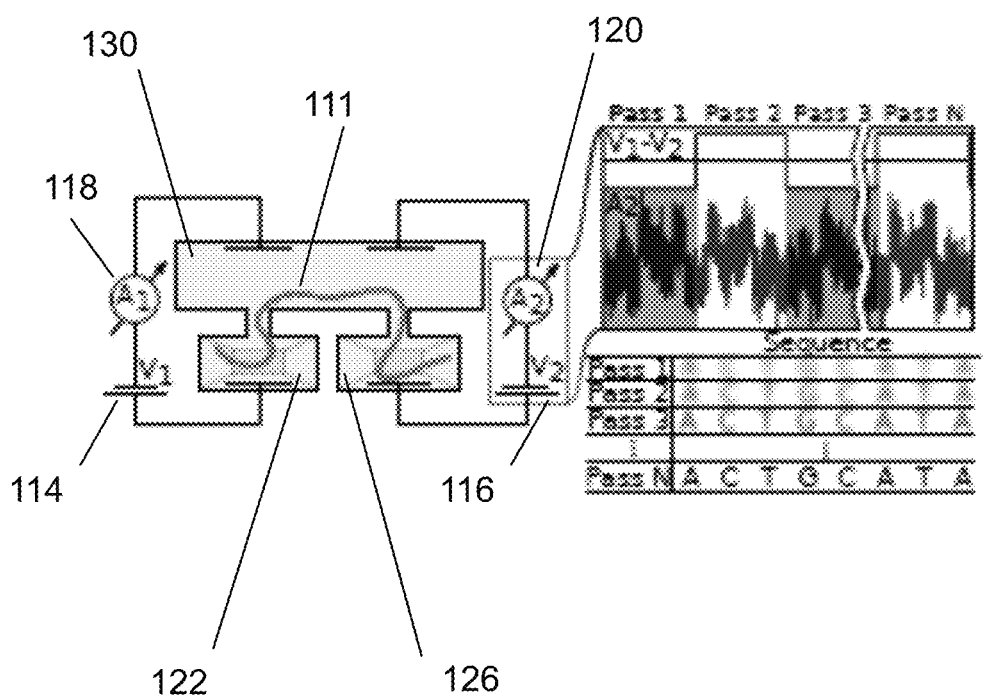
FIG. 1F depicts a simplified cross-sectional view showing certain details (according to an embodiment) of the apparatus 100 (this FIG. also shows an example of multiple passes to sequence a molecule)

Referring now to FIG. 1F, this depicts a simplified cross-sectional view showing certain details of the apparatus 100 (this FIG. also shows an example of multiple passes to sequence a molecule).

Figure 2:
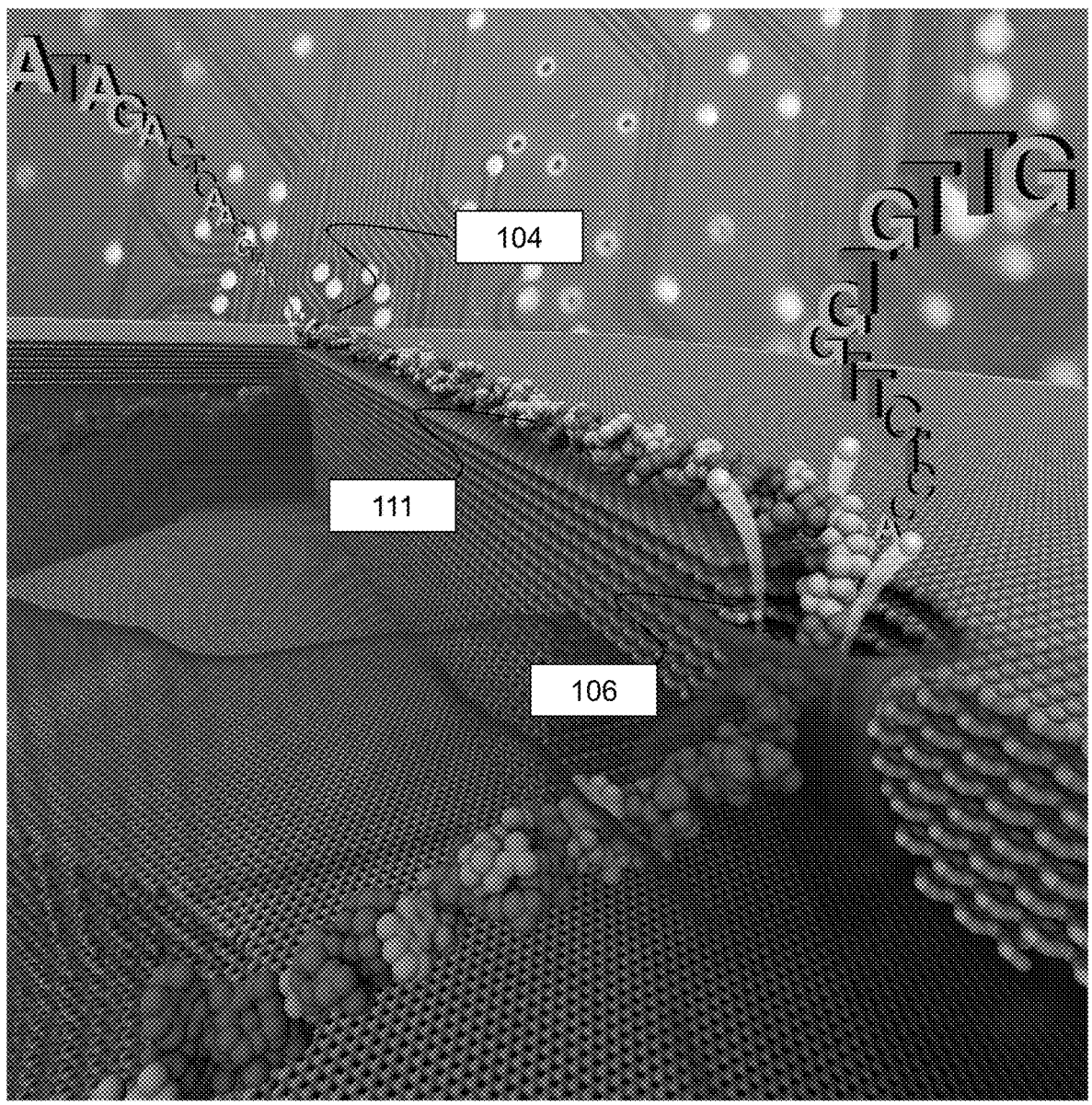
FIG. 2 depicts certain details (according to an embodiment) of the apparatus 100 (this FIG. shows a simplified partially cut-away view depicting molecule 111 extending from pore 104 to pore 106)

Referring now to FIG. 2, this depicts certain details of the apparatus 100 (this FIG. shows a simplified partially cut-away view depicting molecule 111 extending from pore 104 to pore 106).

Figure 3:
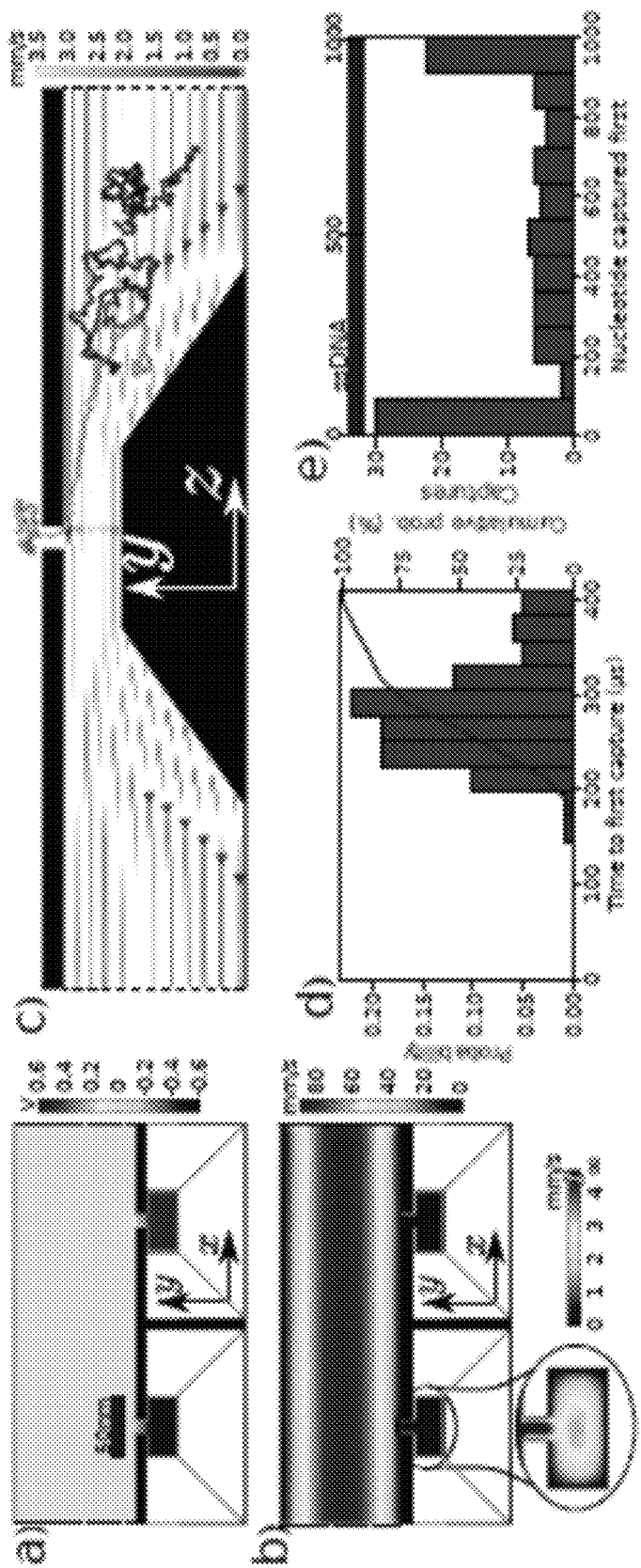
FIG. 3 depicts certain details (according to an embodiment) of statistics of ssDNA capture.

Referring now to FIG. 3, this depicts certain details (according to an embodiment) of statistics of ssDNA capture. More particularly, this figure depicts:
  (a, b) Electrostatic potential (panel a) and fluid flow velocity (panel b) in the x-y cross section of the double-nanopore system. The cross section passes through the two nanopores. The inset illustrates the fluid flow inside the first delivery channel.
  (c) Snapshots illustrating typical conformations of ssDNA (at 0 µs, black; 232 µs, blue; and 307 µs, green) during a nanopore capture in the first delivery channel. The streamlines illustrate the local direction and the magnitude of the solvent flow.
  (d) Normalized distribution of the time elapsed from the start of the simulation until the nanopore capture. The distribution was obtained from the analysis of 100 independent simulations that differed from one another by the initial conformation of ssDNA. The cumulative probability of nanopore capture (plotted at the right axis) reaches 100%; that is, all 100 molecules were captured.
  (e) Probability of first ssDNA capture occurring at the specified site along the DNA molecule.

Figure 4:
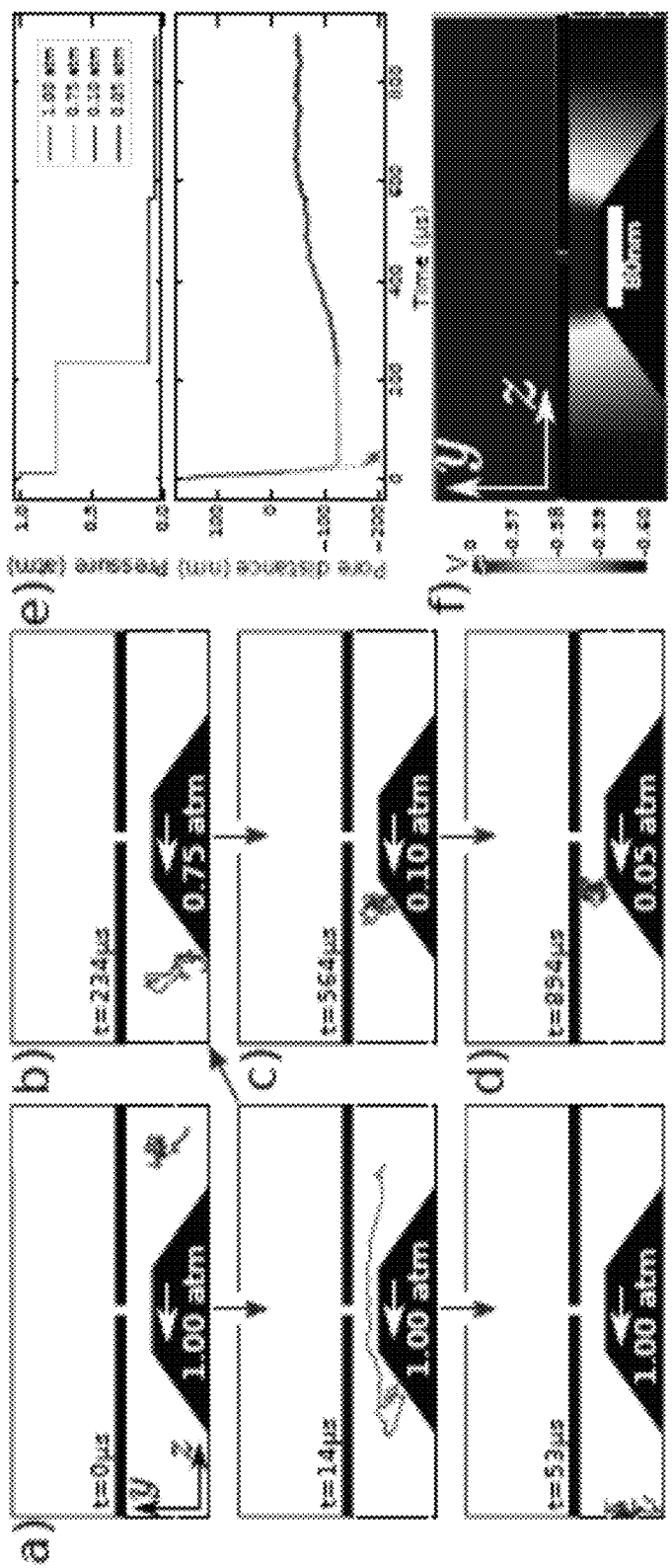
FIG. 4 depicts certain details (according to an embodiment) of trapping molecules that missed the nanopore entrance.

Referring now to FIG. 4, this depicts certain details (according to an embodiment) of trapping molecules that missed the nanopore entrance. More particularly, this figure depicts:
  (a) Snapshots illustrating ssDNA motion through the first delivery channel under $\Delta p_1$=1 atm.
  (b) After 14 µs at $\Delta p_1$=1 atm, $\Delta p_1$ was reduced to 0.75 atm for 220 µs.
  (c) After 220 µs at $\Delta p_1$=0.75 atm, $\Delta p_1$ was reduced to 0.1 atm for 330 µs.
  (d) After 330 µs at $\Delta p_1$=0.1 atm, $\Delta p_1$ was reduced to 0.05 atm for another 330 µs.
  (e) Difference between the inlet and outlet pressure ($\Delta p_1$, top) and the distance between the DNA's center of mass (bottom) and the nanopore as a function of simulation time.
  (f) Distribution of the electrostatic potential in the delivery channel.

Figure 5:
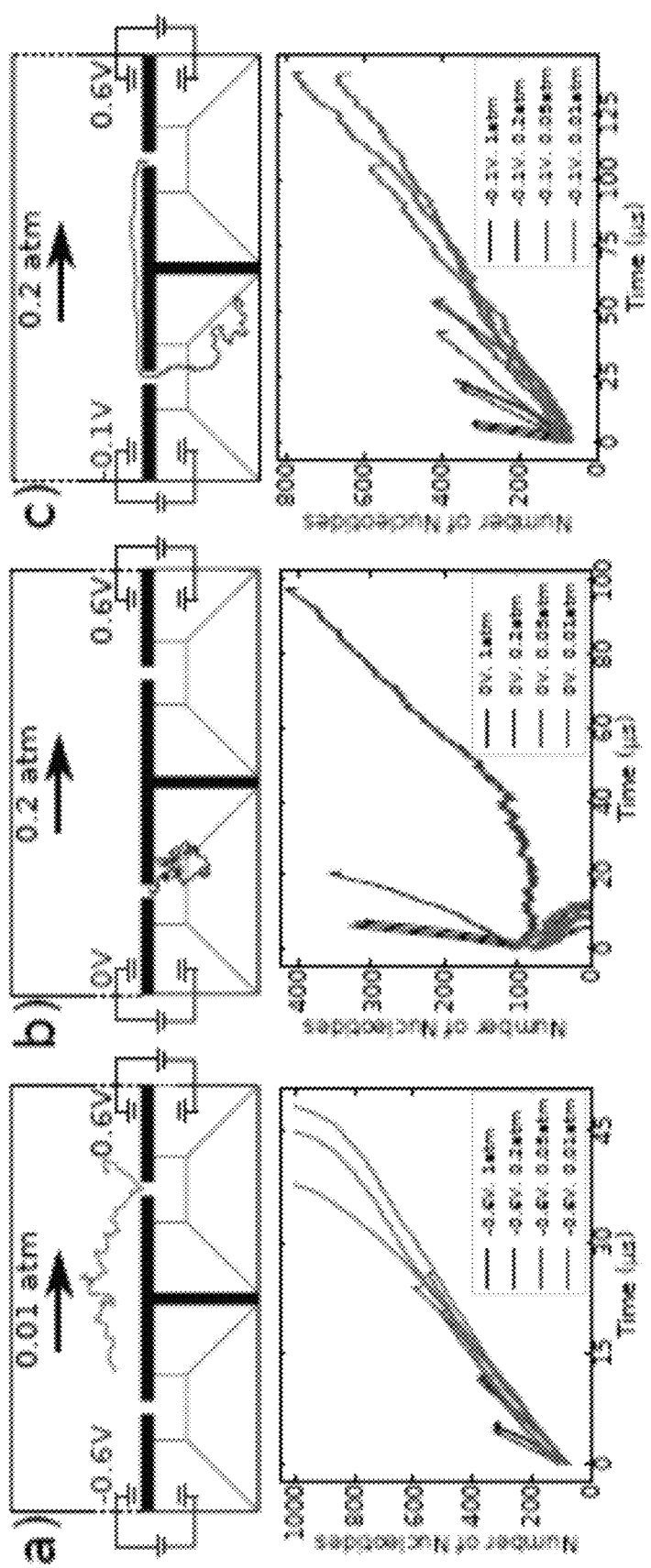
FIG. 5 depicts certain details (according to an embodiment) of conditions affecting the second nanopore capture.

Referring now to FIG. 5, this depicts certain details (according to an embodiment) of conditions affecting the second nanopore capture. More particularly, this figure depicts:
  (a-c) Number of DNA nucleotides in the flow chamber versus simulation time for $V_1$=−600 (panel a), 0 (panel b), and −100 (panel c) mV and the four values of $\Delta p_{ch}$ indicated by the color of the lines. Three independent simulations were carried out for each combination of $V_1$ and $\Delta p_{ch}$. All simulations started from three different initial configurations of ssDNA, each of which was end-threaded through the first nanopore.

Figure 6:
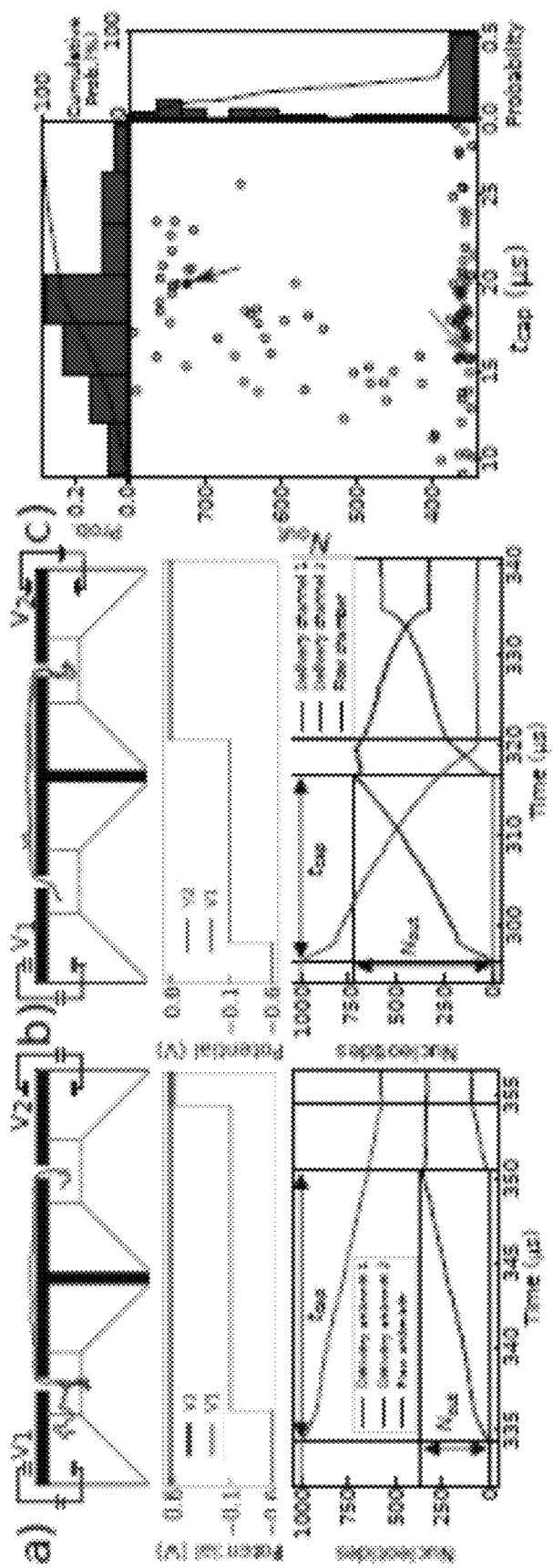
FIG. 6 depicts certain details (according to an embodiment) of statistics of second pore capture.

Referring now to FIG. 6, this depicts certain details (according to an embodiment) of statistics of second pore capture. More particularly, this figure depicts:
  (a, b) Voltage bias (top) and number of DNA nucleotides in the delivery channels and flow chamber (bottom) versus simulation time for end-threaded capture (panel a) and for folded capture (panel b). The time between captures is denoted by $t_{cap}$, and the number of nucleotides in the flow chamber at the time of second capture, by $N_{out}$. The images illustrate the DNA conformation 4 µs after second capture, when $V_1$ is changed to 0.6 V. These times are denoted with a dashed line.
  (c) Scatter plot of $N_{out}$ versus $t_{cap}$ for all 100 simulations. The simulations marked with green and blue arrows are the ones shown in panel a and b, respectively. The histograms show the distribution of the $t_{cap}$ (top) and $N_{out}$ (right) values. The cumulative probability of double-nanopore nanopore capture reaches 100%; that is, all 100 molecules were simultaneously captured in both nanopores.

Figure 7:
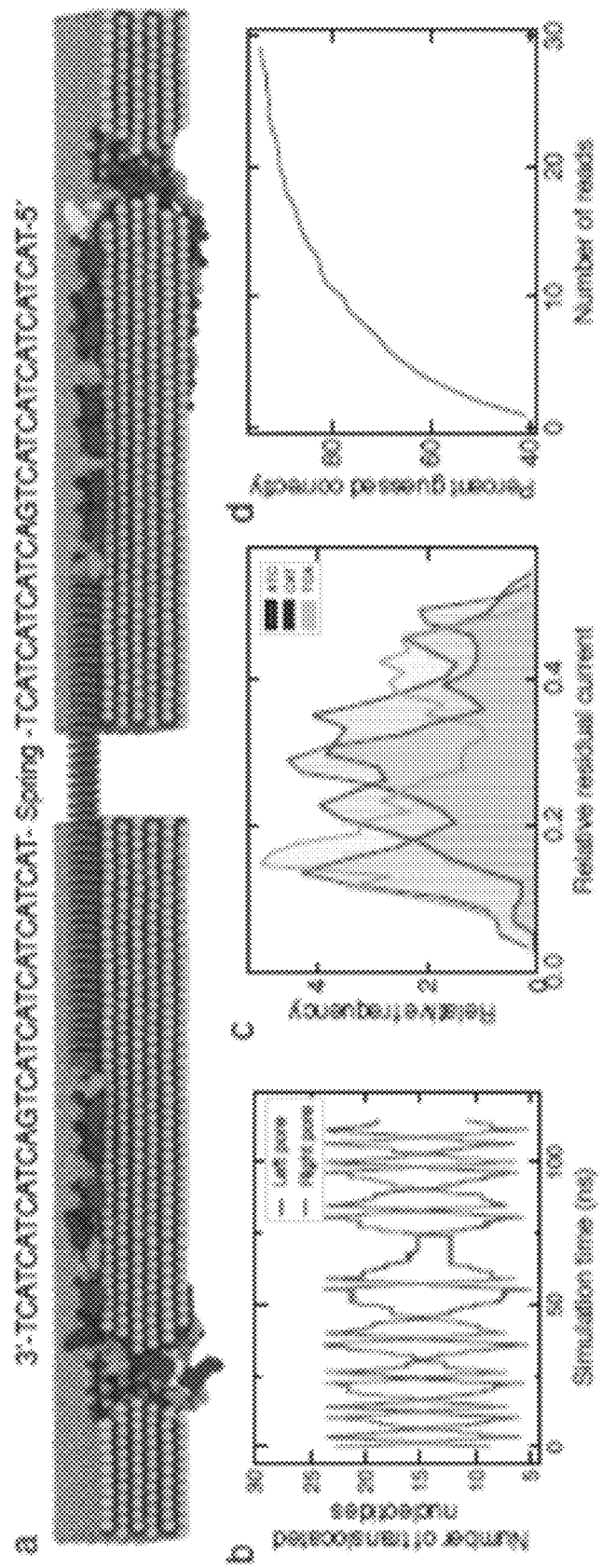
FIG. 7 depicts certain details (according to an embodiment) of infinite-depth sequencing of the same DNA molecule by double-nanopore flossing.

Referring now to FIG. 7, this depicts certain details (according to an embodiment) of infinite-depth sequencing of the same DNA molecule by double-nanopore flossing. More particularly, this figure depicts:
  (a) Illustration of the simulation system, where a fragment of ssDNA is threaded through two solid-state nanopores in a six-layer boron-nitride membrane. A virtual spring (gray) connects the DNA from two simulation systems, coupling DNA motion through both nanopores. The DNA has the repeat-triple sequence. Water and ions are not shown for clarity. DNA flossing is produced by alternatively applying a 10 V bias to either left or right pore.
  (b) Number of DNA nucleotides translocated through each nanopore.
  (c) Distribution of residual ionic current for the three-nucleotide triplet present in the nanopore. Currents were computed using the steric exclusion model (see, e.g., Reference 51).
  (d) Effect of repeat reads of a triplet (due to multiple passes through the pore) on the probability of guessing the correct triplet solely from the relative residual current.

Figure 8:
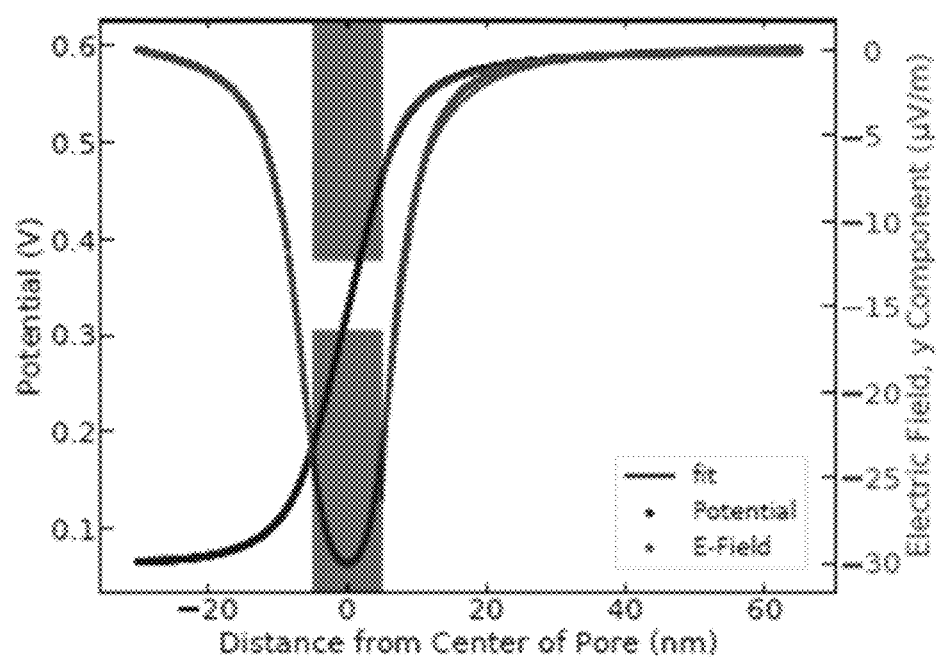
FIG. 8 depicts certain details (according to an embodiment) of electric potential and electric field along the axis of the first pore.

Referring now to FIG. 8, this depicts certain details (according to an embodiment) of electric potential and electric field along the axis of the first pore. It is seen that they each fit the expected functional forms $1/r$ and $1/r^2$, respectively.

Figure 9:
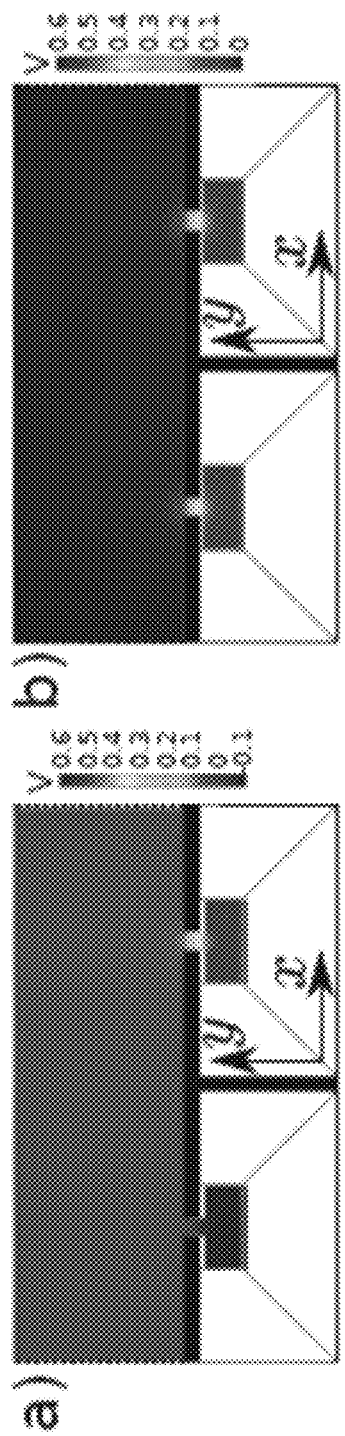
FIG. 9 depicts certain details (according to an embodiment) of the electrostatic potential in the x-y cross section passing through the two nanopores.

Referring now to FIG. 9, this depicts certain details (according to an embodiment) of the electrostatic potential in the x-y cross section passing through the two nanopores. More particularly, this depicts the electrostatic potential in the x-y cross section passing through the two nanopores right before (a), $V_1=-100$ mV; $V_2=600$ mV, and right after (b), $V_1=V_2=600$ mV, the second nanopore capture.

Figure 10:
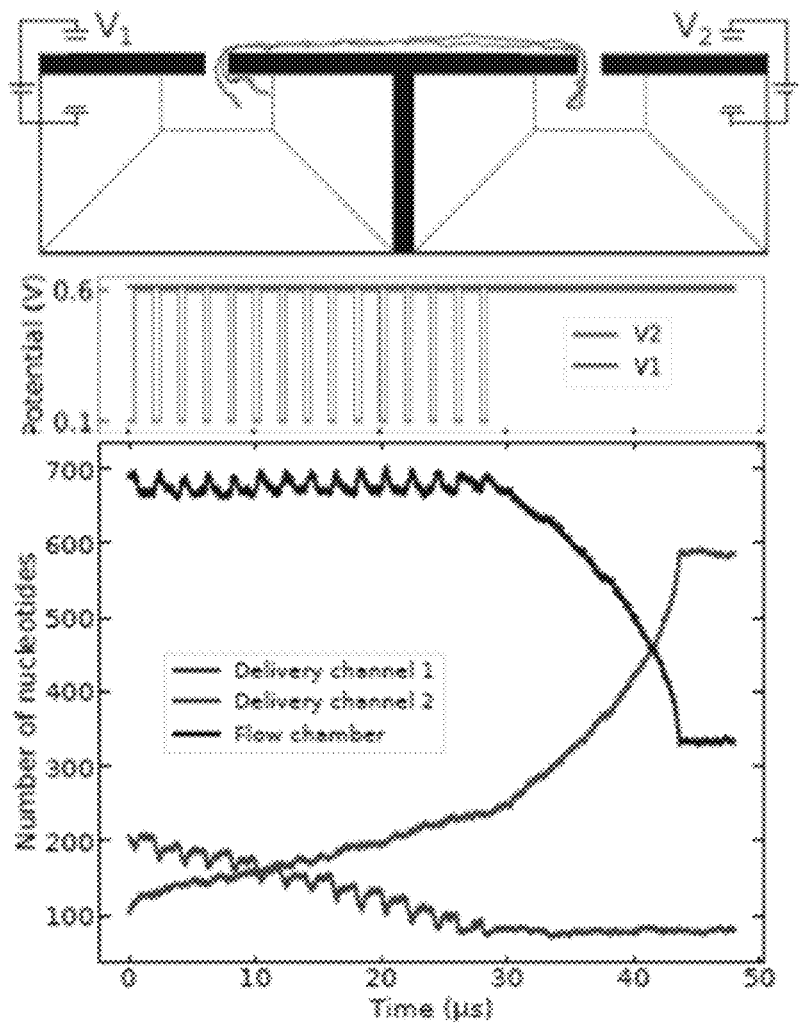
FIG. 10 depicts certain details (according to an embodiment) of DNA captured with both ends in the same pore.

Referring now to FIG. 10, this depicts certain details (according to an embodiment) of DNA captured with both ends in the same pore. To obtain this conformation, the electrostatic potentials were switched to $V_1=V_2=0.6V$ sooner than the 4 μs usually waited. For this conformation, one of its ends can be brought out of the first pore and into the second by periodically pulsing the first pore's potential in the manner shown.

Figure 11:
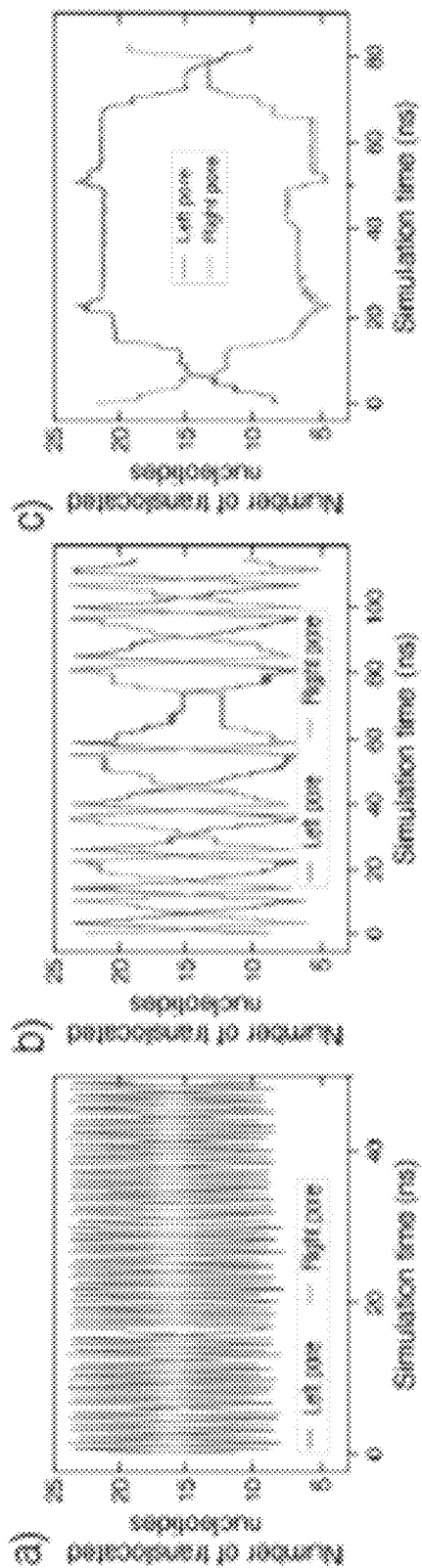
FIG. 11 depicts certain details (according to an embodiment) of number of DNA nucleotides translocated through each nanopore during all-atom MD simulations of the ssDNA flossing.

Referring now to FIG. 11, this depicts certain details (according to an embodiment) of number of DNA nucleotides translocated through each nanopore during all-atom MD simulations of the ssDNA flossing. More particularly, this depicts number of DNA nucleotides translocated through each nanopore during all-atom MD simulations of the ssDNA flossing carried out under 20 V (panel a), 10 V (panel b) and 5 V (panel c) magnitude of the transmembrane bias. FIG. 7(a) shows the simulation system. Data in FIG. 11(b) are the same as in FIG. 7(b).

Figure 12:
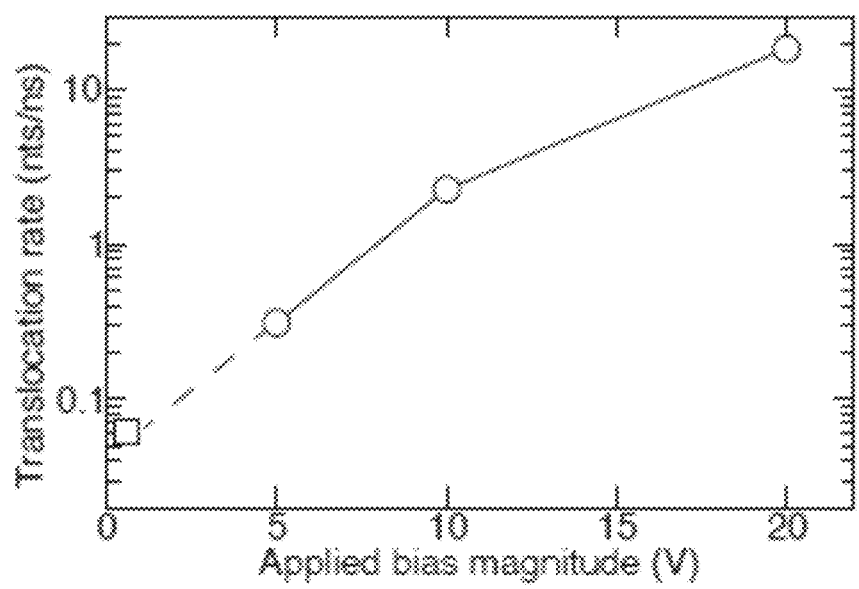
FIG. 12 depicts certain details (according to an embodiment) of the average rate of nucleotide transport observed in the all-atom MD simulations.

Referring now to FIG. 12, this depicts certain details (according to an embodiment) of the average rate of nucleotide transport observed in the all-atom MD simulations of ssDNA flossing through a double hBN nanopore system, FIG. 11 versus the magnitude of the voltage bias (open circles). The square symbol indicates the average translocation rate, ~0.05 nts/s, observed in certain previous all-atom simulations of ssDNA transport through a single, two-layer graphene nanopore at 500 mV bias (see, e.g., Reference 53). Lines are guides to the eye.

Figure 13:
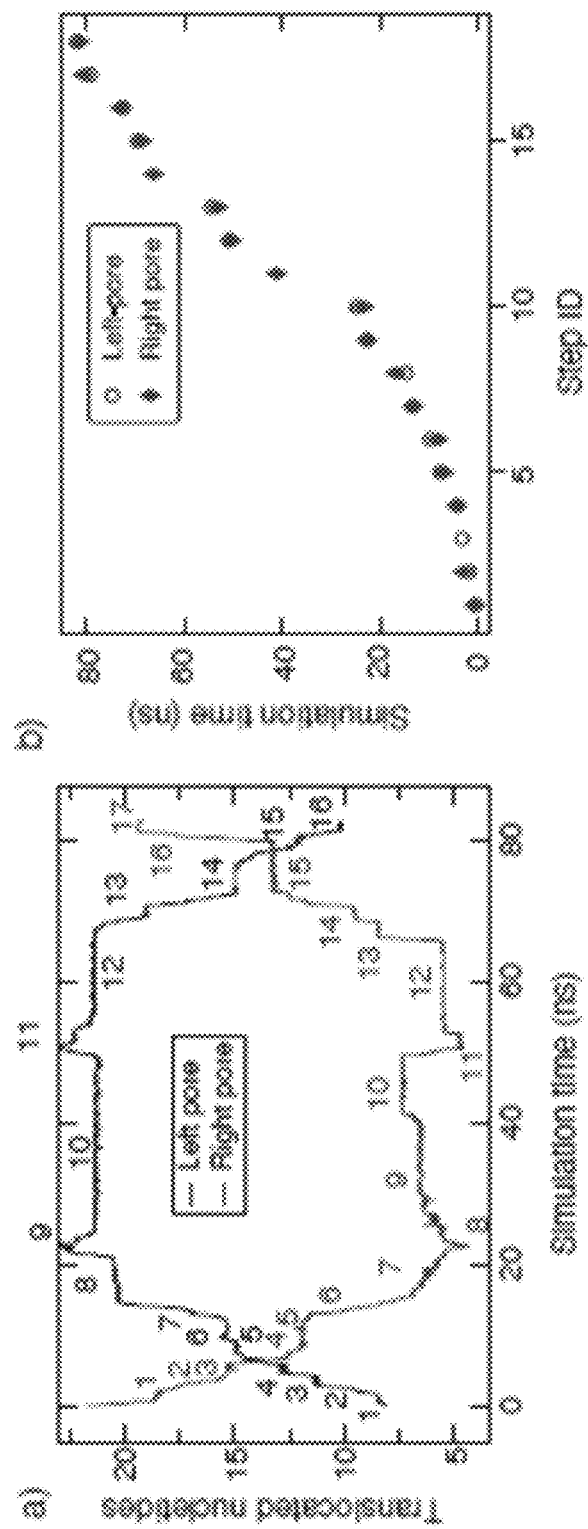
FIG. 13 depicts certain details (according to an embodiment) of correlated stepwise displacement of an ssDNA strand through the nanopores of a double-nanopore hBN system.

Referring now to FIG. 13, this depicts certain details (according to an embodiment) of correlated stepwise displacement of an ssDNA strand through the nanopores of a double-nanopore hBN system. More particularly:
  (a) Number of DNA nucleotides translocated through each nanopore during all-atom MD simulations carried out at a 5 V bias (same as in FIG. 11(c)). The numbers shown in black and red count the number of stepwise displacements undertaken by the ssDNA strand through each nanopore. The steps were assigned through visual inspection; steps of less than one nucleotide or lasting less than 1 ns were not considered in the analysis.
  (b) The simulation time at which each stepwise displacement took place in each of the two nanopores.

Figure 14:
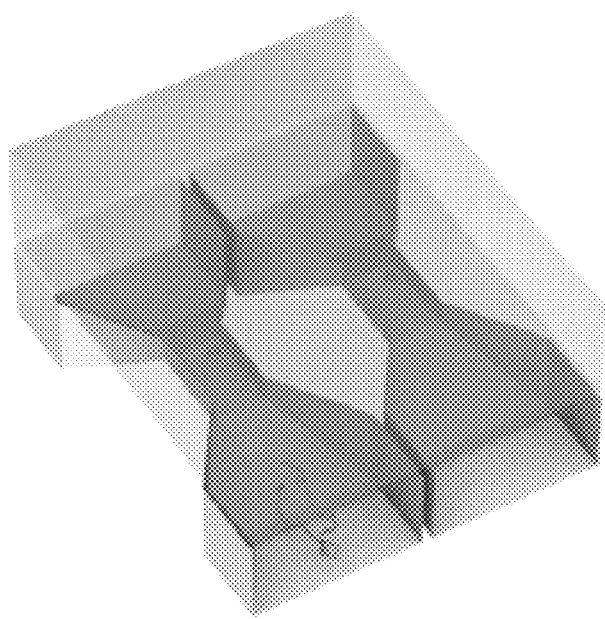
FIG. 14 depicts certain details (according to an embodiment) related to capture, threading, and sequencing of a single-stranded DNA molecule in a nanofluidic double nanopore system.

Referring now to FIG. 14, this depicts certain details (according to an embodiment) related to capture, threading, and sequencing of a single-stranded DNA molecule in a nanofluidic double nanopore system.

Figure 15:
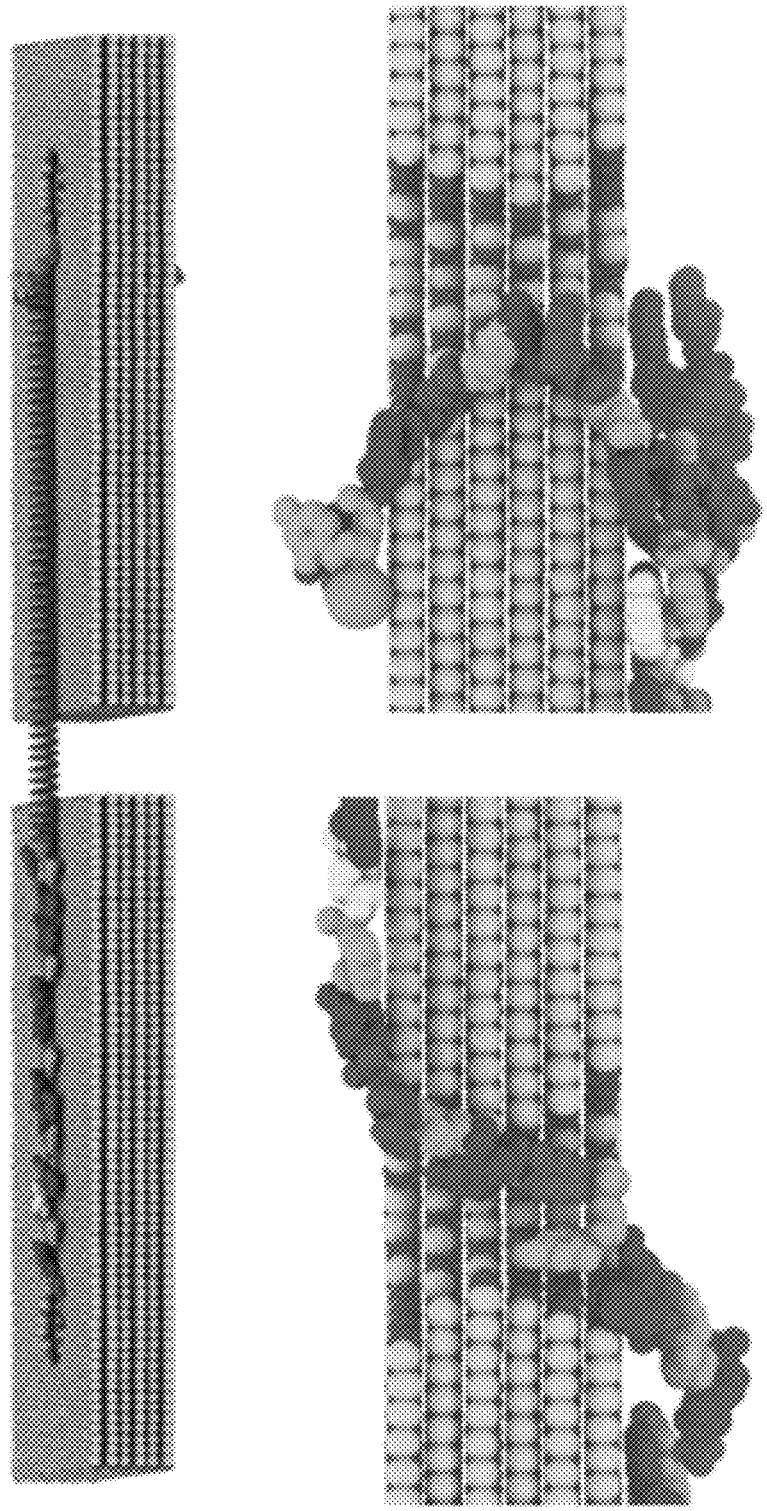
FIG. 15 depicts certain details (according to an embodiment) related to an all-atom MD simulation of repeat flossing of ssDNA through a double nanopore system.

Referring now to FIG. 15, this depicts certain details (according to an embodiment) related to an all-atom MD simulation of repeat flossing of ssDNA through a double nanopore system. More particularly, the bottom left and right screenshots of an animation show a cut-away, zoomed in view of individual nanopores of the double nanopore system shown at the top. The animation illustrates the simulation trajectory featured in FIG. 7.

Figure 16:
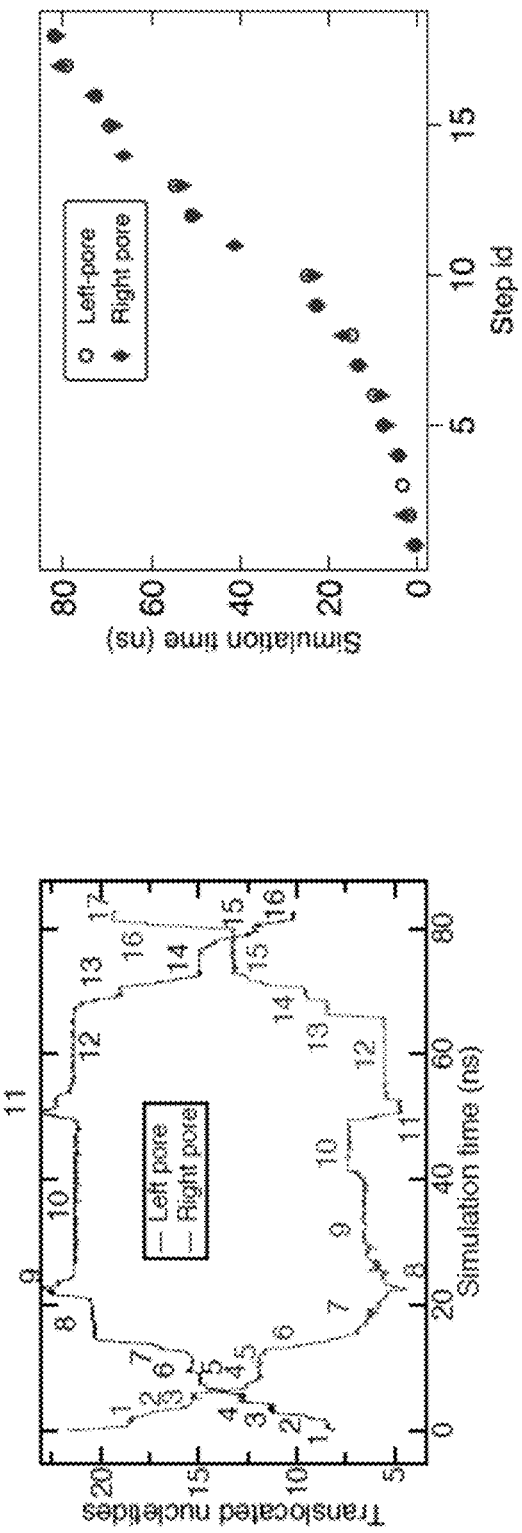
FIG. 16 depicts certain details (according to an embodiment) related to translocation steps being correlated.

Referring now to FIG. 16, this depicts certain details (according to an embodiment) related to translocation steps being correlated. More particularly, the left panel shows simulation time (x-axis) versus translocated nucleotides (y-axis) and the right panel shows step id (x-axis) versus simulation time (y-axis).

Figure 17:
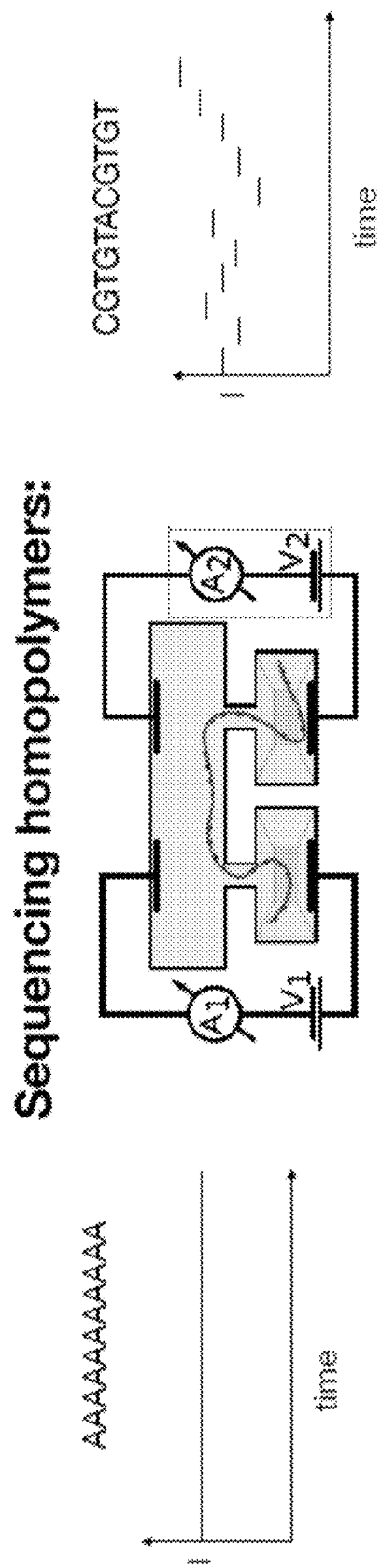
FIG. 17 depicts certain details (according to an embodiment) related to sequencing homopolymers.

Referring now to FIG. 17, this depicts certain details (according to an embodiment) related to sequencing homopolymers. More particularly, the middle panel shows a cross-sectional view of a system according to an embodiment, the left panel shows an example sequence (corresponding to the left pore of the middle panel) of time (x-axis) versus current (y-axis), and the right panel shows an example sequence (corresponding to the right pore of the middle panel) of time (x-axis) versus current (y-axis).

As described herein, various embodiments provide systems and methods for high-fidelity capture, threading, and infinite-depth sequencing of single nucleic acid molecules.

As described herein, various embodiments provide systems and methods for sequencing homopolymer stretches (parts of the molecule consisting of the same nucleotide type) of nucleic acid molecules.

As described herein, various embodiments provide nanopore sequencing with improved accuracy of raw reads and improved detection of nucleotide modifications.

Described and demonstrated herein through simulations is a nanofluidic system (according to an embodiment) for loading and threading DNA strands through a double-nanopore setup with nearly 100% fidelity. In one example, the high-efficiency loading can be realized by using hourglass-shaped channels (e.g., side channels) that not only deliver the molecules to the nanopore but also retain molecules that missed the nanopore at the first passage to attempt the nanopore capture again. The second nanopore capture can be facilitated by an orthogonal microfluidic flow that unravels the molecule captured by the first nanopore and delivers it to the capture volume of the second nanopore.

Demonstrated herein is utility of the double nanopore system (according to various embodiments) for DNA sequencing by simulating repeat back-and-forth motion ("flossing") of a DNA strand through the double nanopore system. It is shown herein that repeat exposure of the same DNA fragments to the nanopore sensing volume considerably increases accuracy of the nucleotide sequence determination, and that correlated displacement of ssDNA through the two nanopores can facilitate recognition of homopolymer fragments.

Demonstrated herein is utility of the double nanopore system (according to various embodiments) for determining the length of homopolymer fragments passing through one nanopore by counting the number of current steps produced by the heterogeneous sequence fragment of the same molecule passing through the other nanopore.

As described herein, nanopore sensing (see, e.g., References 1,2) and sequencing (see, e.g., References 3,4) can rely on the partial blockade of ionic current flowing through a nanopore for detection and identification of biomolecules (see, e.g., Reference 5). For globular biomolecules, which includes the majority of folded proteins and some RNA, a nanopore sensor can operate similar to a Coulter counter (see, e.g., Reference 6), where the passage of individual biomolecules produces ionic current transients characterized by well-defined depth and width (see, e.g., Reference 7). Nanopore translocation of a nucleic acid polymer produces much more complex signatures (see, e.g., References 8,9), which nevertheless can be transcribed (see, e.g., Reference 10) into the nucleotide sequence of the polymer (see, e.g., Reference 11).

One problem with certain conventional nanopore sensing, however, is that one gets to measure the signal from a passing analyte only once, which severely limits fidelity of the analyte identification. Two types of approaches have been described to extend the exposure of an analyte to the nanopore current characterization: reducing the speed of the nanopore translocation or capturing the same molecule more than once by a nanopore. While many diverse approaches have been devised to transiently arrest nanopore transport (see, e.g., References 12-16), measuring a nanopore signal from the same molecule has typically been limited to recapturing the molecule by the same nanopore (see, e.g., Reference 17) or to passing the same molecule sequentially through two nanopores (see, e.g., References 18-20).

A double-nanopore system (see, e.g., Reference 21) can, potentially, enable multiple reads of the sequence of a nucleic acid polymer (see, e.g., References 22,23) or repeat measurements of the current blockade from the same protein bound to DNA (see, e.g., References 24,25). In such a system, the electrophoretic force of the two nanopores creates a tug-of-war condition (see, e.g., Reference 26), straightening the molecule confined between the nanopores and allowing the translocation direction to be controlled by a minute difference in the magnitude of the forces exerted by the two nanopores (see, e.g., Reference 21). Believed to be first demonstrated in the form of a mechanical trap (see, e.g., Reference 21), the tug-of-war control over DNA motion was also realized in a double-barrel capillary system (see, e.g., References 24,27) and in a solid-state device (see, e.g., Reference 28) integrated with a field-programmable gate array enabling active control of the DNA translocation process (see, e.g., Reference 29).

One potential problem with using a double-nanopore system for sequencing and/or sensing applications is the need to capture and thread a DNA or any other molecule not just through one but through two nanopores. Improving the rate of nanopore capture has long been recognized as a critical factor enabling practical applications of nanopore sensing with major breakthroughs involving the use of a salt gradient (see, e.g., Reference 30), dielectrophoretic forces (see, e.g., References 31,32), or membrane tethering of ssDNA (see, e.g., References 11,33). Systems have been designed to filter and sort DNA molecules according to their size (see, e.g., Reference 34) or to alter DNA conformation prior to entering a nanopore (see, e.g., Reference 35). Controlled DNA delivery has been realized using a glass capillary (see, e.g., Reference 36) and an optofluidic device (see, e.g., Reference 37), whereas both side solvent flow (see, e.g., Reference 38) and conical confinement (see, e.g., Reference 39) have been explored to increase efficiency of nanopore capture.

Various embodiments described herein demonstrate through coarse-grained and all-atom molecular dynamics simulations a double-nanopore system for capturing and threading single-stranded DNA (ssDNA) molecules with 100% efficiency and show how multiple reads from the same molecule improve fidelity of DNA sequence identification. Such a combination of high-fidelity loading and repeat sequencing of the same molecule (according to various embodiments) can offer considerable improvements in the performance of the nanopore sequencing method with regard to nucleotide identification at a truly single-molecule level.

Reference will now be made to certain Results according to an embodiment. More particularly, a double-nanopore system (according to an embodiment) includes three solution-filled volumes: two parallel delivery channels and a cross-flow chamber separated from the delivery channels by a thin membrane (see, e.g., FIG. 1E). Each delivery channel is connected to the flow chamber through a nanopore located in the narrowest section of the delivery channel. The DNA is introduced at the rectangular section of the first delivery channel (see, e.g., FIG. 1E—view (a)). The DNA is then threaded through the first and then the second nanopore with 100% efficiency, guided by the pressure and voltage differences at the inlets and outlets of the solution-filled volumes. In a study described herein, the specific geometry of the device and the operating conditions were chosen in order to keep the simulations feasible and to examine the limits of this double-nanopore capture approach. A consequence of this is that the procedure described below may be experimentally difficult to replicate exactly. Nevertheless, it is emphasized that this double-nanopore capture approach (according to an embodiment) is robust to the kinds of changes that experimental considerations would require, and comments will be made on these changes as they arise.

Still referring to certain Results according to an embodiment (see, e.g., FIG. 1E—views (a)-(e) and FIG. 14), illustrated is a typical outcome of a coarse-grained molecular dynamics (MD) simulation of 1 kbp ssDNA threading. Starting from a configuration shown in FIG. 1E—view (a), a pressure difference of 0.05 atm across the first delivery channel ($\Delta p_1$) transports the solvent along with the DNA toward the first nanopore. A −600 mV difference of the electric potential ($V_1$) between the inlet/outlet boundaries of the first delivery channel and the electrically grounded flow chamber captures the DNA from the first delivery channel into the first nanopore (see FIG. 1E—views (a)-(b)). Driven by a pressure difference of 0.2 atm ($\Delta p_{ch}$), the solvent flow in the flow chamber guides the end of the DNA captured by the first nanopore toward the second nanopore, where a voltage difference of 600 mV ($V_2$) promotes the capture of the DNA by the second nanopore (see FIG. 1E—views (c)-(d)). Having the DNA molecule threaded simultaneously through both nanopores, further motion of the DNA is halted by setting the voltage in the two delivery channels to the same positive value ($V_1=V_2=600$ mV), which straightens the DNA confined between the two nanopores (see FIG. 1E—view (e)). From this configuration, the DNA molecule can be flossed back and forth through the two nanopores by a voltage differential, $V_1-V_2$, and can be eventually removed from the double-nanopore system by setting a nonzero pressure difference ($\Delta p_2$) across the second delivery channel.

Still referring to certain Results according to an embodiment, characterized are the fidelity of the nanopore capture and threading by repeating the simulation 100 times starting from different initial conformations of 1 kbp ssDNA. This DNA length was chosen as it is close to the minimum value that a device of the given nanopore spacing could reliably handle. If the middle of the DNA is caught at the first nanopore, the DNA nearly exits the first nanopore as it enters the second. This would not happen (in this embodiment) for DNA significantly longer than 1 kbp and such molecules would be captured with greater ease. Note that the mechanism of high-fidelity capture and threading (according to various embodiments) would also work for double-stranded DNA and RNA/DNA hybrid constructs upon scaling up the device dimensions to account for a larger persistence length. The choice of simulation conditions described herein was dictated by a ~1 V upper bound on the magnitude of voltage bias differential, with 600 mV being a typical value used in the double-nanopore capture experiments (see, e.g., References 28,29). For the pressure differentials, the 0.01 to 1 atm range was explored, which is also experimentally accessible (see, e.g., Reference 40). Through all the simulations described herein, the electric potential of the second delivery channel, $V_2$, was kept constant to minimize the changes in conditions required for the realization of the threading process. Thus, the capture process in the simulation described herein was controlled by the voltage of the first delivery channel, $V_1$. Note that because the coarse-grained simulations described herein neglect friction between the pore walls and the DNA, the DNA transport rates reported below should be regarded as the fast transport limit. The transport in an equivalent experimental device is expected to be slower.

Still referring to certain Results according to an embodiment, reference will first be made to characterization of the statistics of ssDNA capture by the first nanopore. Illustrated (see, e.g., FIG. 3—panels (a)-(b)) are the distribution of the electrostatic potential and of the fluid flow velocity in a double-nanopore system (according to an embodiment) under conditions that promote the first capture. The electrostatic potential in the first and the second delivery channels approaches the −/+600 mV values prescribed at the channels' inlets and outlets. The solvent flow through the flow chamber has the expected laminar profile, whereas the flow profile in the delivery channels is more peculiar, with the fluid having a higher velocity at the channel's constriction, where the nanopore is located, than at the inlet/outlet surfaces. FIG. 3—panel (c) provides a more detailed view of the flow profile in the first delivery channel along with three representative snapshots of ssDNA conformation realized during a typical simulation of ssDNA capture.

The shear force of the nonuniform fluid flow combined with the gradient of the electric potential (see, e.g., FIG. 8) contributes to highly efficient capture of ssDNA by the nanopore. Although the time elapsed from the beginning of each simulation until the nanopore capture was found to have a broad distribution (see, e.g., FIG. 3—panel (d)), the DNA capture was observed in all 100 simulations, meaning that the cross-channel system (according to an embodiment) captures ssDNA with 100% efficiency. Interestingly, observed was a pronounced preference for ssDNA to be captured at its ends, with about half of all ssDNA capture events starting with capturing a DNA fragment located within the first hundred nucleotides from the DNA's end (see, e.g., FIG. 3—panel (e)). Similar preference for end-capture was experimentally observed in single-nanopore experiments performed using double-stranded DNA (see, e.g., Reference 41).

The reported 100% efficiency of ssDNA capture has been made possible in part by the pressure difference that forced the solvent through the first delivery channel. While lowering that pressure would make it take longer for the DNA to reach the first pore, increasing the pressure could have more serious consequence: it would increase the chance for DNA to miss its opportunity to enter the nanopore. This was demonstrated directly in a simulation carried out under $\Delta p_1 = 1$ atm (see, e.g., FIG. 4—panel (a)), where it can be seen that the ssDNA is stretching and missing the nanopore entrance. Interestingly, when the simulation was restarted midway from the 1 atm trajectory at a lower, 0.75 atm pressure, the DNA was still seen missing the nanopore entrance but the DNA was not carried away from the nanopore by the flow (see, e.g., FIG. 4—panel (b)). Rather, it became suspended a fixed distance past the nanopore entrance. Continuing the simulation at even lower pressure values, at 0.1 atm (see, e.g., FIG. 4—panel (c)), and then at 0.05 atm (see, e.g., FIG. 4—panel (d)), confirmed this behavior: at each pressure value, the DNA was seen to adopt a new equilibrium location past the nanopore, moving closer to the nanopore entrance at lower pressure. FIG. 4—panel (e) describes this behavior quantitatively by showing the pressure and the z-coordinate of the DNA center of mass as a function of simulation time. This behavior is attributed to a small yet apparently sufficient electric field that leaks out from the nanopore and into the delivery channel (see, e.g., FIG. 4—panel (f)), and exerts a force on the DNA that cancels the force of the solvent flow. Thus, even if a DNA molecule misses the nanopore entrance (which, in experiment, would be registered as a shallow blockade of the nanopore current), the molecule is not lost and can be pulled back by lowering the pressure in the delivery channel.

Still referring to certain Results according to an embodiment, reference will now be made to the second nanopore capture, which is facilitated by the fluid flow through the flow chamber. The DNA's capture by the first nanopore is registered experimentally as a pronounced blockade of the ionic current flowing through the first nanopore (see, e.g., Reference 29). This event can be used to adjust the experimental conditions to increase the chance of double-nanopore threading. To simplify further analysis, the pressure differential was turned off and the potential was increased to $V_1 = -100$ mV in the first delivery channel 1.5 µs after the first capture. Simply leaving the potential of the first channel at $V_1 = -600$ mV could push the DNA from the delivery channel into the flow chamber faster than the flow could straighten it out, thereby increasing the chance that the DNA will exit the first pore before being captured at the second (see, e.g., FIG. 5—panel (a)). The likelihood of this outcome was exacerbated by a slower flow of solvent in the flow chamber, i.e., lower $\Delta p_{ch}$, values. At the same time, it was found that switching the first potential off ($V_1 = 0$) would create the conditions for the DNA to pull back into the delivery channel under the action of the entropic force (see, e.g., Reference 42) from the rest of the DNA (see, e.g., FIG. 5—panel (b)). The optimal condition for the double nanopore threading in this embodiment was found when the potential of the first delivery channel was not switched off completely but increased to a higher value, from −600 to −100 mV (see, e.g., FIG. 5—panel (c)), exerting a force sufficient to counteract the entropic pull back and yet not too large to generate extra slack of ssDNA in the flow chamber.

In the above simulations, it was decided to wait only 1.5 µs after the first capture before increasing the voltage to −100 mV in order to investigate the situation where entropic pullback of the DNA could result in a failed capture. Although only tens of nucleotides translocated into the flow chamber within those 1.5 µs, the DNA did not pull out, ensuring that pullback will not occur for longer reaction times either. A practical reason for changing the potential after the first capture would be to decrease the slack in the DNA prior to the second capture. However, even if the potential is not changed, the second capture still occurs successfully (see, e.g., FIG. 5—panel (a)). It is noted that turning off the pressure in the first delivery channel after ~1.5 µs is not required for successful experimental implementation. This is apparent from FIG. 4—panels (b)-(d), showing the fluid force on the DNA in the constriction to balance the force of the electric field leaking out from the nanopore. The field inside the nanopore is about 2 orders of magnitude larger than the field leaking out from the nanopore, so keeping the pressure difference on in the first delivery channel will not pull the DNA back from the first nanopore or noticeably affect the process of the second nanopore capture.

In selecting the pressure differential for the flow chamber, an objective was to have a flow that kept the DNA straight and against the chamber wall to maximize the likelihood that it will come near the second pore and be captured. A pressure that is too small introduces slack into the DNA (see, e.g., FIG. 5—panel (a)). On the other hand, a pressure that is too large is also undesirable, because it decreases the time between the two captures without offering a significantly straighter conformation. Using $\Delta p_{ch}$, =0.2 atm in the simulations was observed to sidestep all of the above complications (see, e.g., FIG. 5—panel (c)).

Having determined the optimal condition for capturing ssDNA by the second nanopore, the statistics of the second nanopore capture are now characterized. The entrance of a DNA strand into the second nanopore is experimentally registered as a drop of the ionic current flowing through the second nanopore. Detection of such a drop will trigger a further adjustment of potential $V_1$, which is set in the simulation to the same value as $V_2$, +600 mV, 4 μs after the second capture has occurred. Additionally, all pressure differentials were set to zero. FIG. 9 shows the distribution of the electrostatic potential in the double-nanopore system (according to an embodiment) immediately before and after the second nanopore capture. It was found that second nanopore captures are naturally categorized as either end-first or folded capture. The type of capture was determined by monitoring the number of nucleotides in each of the three channels. For end-first capture, the number of nucleotides in the flow chamber rises steadily after first capture until the maximum value of roughly 330 nucleotides are inside (see, e.g., FIG. 6—panel (a)). At this point, the end of the DNA molecule is captured by the second nanopore, and the number of nucleotides in the second delivery channel rises for 4 μs, after which the electrostatic potentials are set to $V_1=V_2=+600$ mV, and the DNA is held in place with no subsequent change to the number of nucleotides in any of the chambers.

For folded captures, it was seen that nucleotides exit the first delivery channel and enter the flow chamber at about twice the rate seen in end-first capture (see, e.g., FIG. 6—panel (b)). This signifies that the DNA molecule has folded somewhere along its length to enter the first nanopore and that there are two fragments of the same ssDNA molecules in the first nanopore after first capture. At the time of second capture, this DNA molecule enters the second nanopore, again in a folded conformation. After 4 μs the electrostatic potentials are set to hold the DNA molecule still, but because one end of the DNA still exists in the flow chamber, significant adjustment is seen to the number of nucleotides in the second delivery channel and flow chamber as the free end of the DNA is pulled through the second nanopore. While the specific location of the DNA nucleotides cannot be easily monitored so closely in experiments, the blockade currents through the nanopores can be measured to deduce the number of DNA strands translocating through each nanopore (see, e.g., References 21,29).

Still referring to certain Results according to an embodiment, in order to understand the frequency of these different capture modes, it was determined for each simulation the time between first and second capture, $t_{cap}$, and the number of nucleotides in the flow chamber at the time of second capture, $N_{out}$. The resulting scatter plot in FIG. 6—panel (c) consists of a flat and linear part. The points at the lower right correspond to those DNA molecules captured by the first nanopore at the end. As the point of first capture begins to shift away from the end, the fluid pressure in the flow chamber quickly straightens out the DNA's fold before it arrives at the second nanopore, resulting in a constant value of $N_{out}$ and a reduced value of $t_{cap}$. However, as the point of first capture shifts further away from the end, the fold in the DNA cannot be fully removed in the flow chamber, resulting in the linear rise of $N_{out}$ beginning in the lower left of the plot. By collapsing the scatter plot into a histogram for the value of $N_{out}$, it is seen that half of the simulations resulted in end-first capture and half in folded capture at the second pore. It is also worth mentioning that, although the time to first capture is not so well-defined because it varies on the order of hundreds of μs, the histogram corresponding to $t_{cap}$ shows that after the first capture the time to second capture varies only on the order of tens of μs and is thus far more predictable.

In the above simulations, the simulation conditions were switched 4 μs after the second capture to ensure that approximately 100 nucleotides translocated into the second delivery channel, preventing entropic pullback that could be caused by the difference in the number of nucleotides in the two delivery channels. If such a rapid change is not achieved experimentally, more DNA will translocate into the second delivery channel and make the DNA pull out even less likely. The solvent flow in the flow chamber, however, was found to produce a deterministic slip (~12.5 nt/μs) of the DNA from the first nanopore to the second even when both voltages were set to +0.6 V. To prevent such slippage, switching off the flow in the flow chamber should be performed in sync with reducing the voltage differential ($V_1$-$V_2$), the precise specifications of which will depend on the reaction time of the nanofluidic system.

For fragments of DNA significantly longer than 1 kbp, it is increasingly likely that both of the ends will still be in the first delivery channel at the end of the double-nanopore capture method (according to an embodiment). Although this did not occur in any of the 100 simulations discussed herein, a scheme was created to remove one end out of the first pore and into the second (see, e.g., FIG. 10). By periodically pulsing the electric potential across the first pore down from 0.6 to 0.1 V to create an imbalance in the tug-of-war, the DNA slips little by little into the second pore until one end of the DNA exits the first pore, resulting in successful capture.

In order to demonstrate the changes experimentalists would have to make to employ such a double-nanopore capture process (according to an embodiment), considered now are the specific changes that would be needed if the nanopore spacing was increased by a factor of 10, to 1700 nm. As far as the second capture is concerned, the most obvious consequence of this change would be that the minimum length of DNA the device could sequence would also increase by a factor of 10. Furthermore, lengthening the flow chamber would make it more resistive to fluid flow. An increased applied pressure could counter this to achieve the desired fluid velocity, but if the device could not be safely put under such a pressure, the cross section of the flow chamber could be increased to reduce its resistance. With regard to the first capture, using longer DNA requires no change to the geometry of the delivery channels. This is apparent by observing the stretched conformation of the DNA in FIG. 3—panel (c). The constriction in the delivery channel serves to accelerate the flow and expand the electric field's reach such that DNA is caught not when the center of mass of the DNA approaches the nanopore but when a segment of the DNA begins to approach the constriction and is then stretched out and caught. This would be how DNA of any length is captured in such a device, and emphasized herein is the importance of replicating such a constriction in experiment. Such funnel like channels can be manufactured using the focused ion beam milling technology (see, e.g., Reference 39).

Still referring to certain Results according to an embodiment, demonstrated now is the utility of a double nanopore system (according to an embodiment) for DNA sequencing by considering a situation where a single DNA molecule is already threaded through two nanopores in a multilayer hexagonal boron nitride (hBN) membrane, (see, e.g., FIG. 7). Although solid-state nanopores have long been recognized as potentially superior replacements for biological nanopores (see, e.g., References 43-45) solid-state nanopore sequencing has remained elusive (see, e.g., References 46,47). The most important problems are speed control and entropic conformational randomness (see, e.g., References 48,49). It is believed that both problems can be resolved using a system (according to an embodiment) of two nanopores in a 2D membrane which provides both speed control by controlling the difference of the voltage drop across the two nanopores and which also drastically decreases the heterogeneity of nucleotide conformations because of the nucleotides' adhesion to the membrane (see, e.g., Reference 50).

For proof-of-principle simulations (according to an embodiment), chosen was a system of two identical 1.5 nm diameter hBN nanopores that were shaped to reproduce the constriction of the MspA nanopore, the first nanopore used to experimentally demonstrate nanopore DNA sequencing (see, e.g., Reference 9). Each of the two all-atom simulation systems contained a fragment of ssDNA of triplet-repeat sequence, similar to that used by Gundlach and coworkers (see, e.g., Reference 9). The two simulations were coupled via a harmonic potential applied to the ends of the DNA, mimicking the experimental situation where the same DNA fragment is captured by two nanopores that are separated by a distance that considerably exceeds the length scale amenable to the all-atom MD method. The DNA translocation back and forth through the double-nanopore system was realized by applying a voltage bias alternatively to each simulation system, reversing the translocation direction when the strand's end reached the edge of the simulation system. Because of ssDNA adhesion to the hBN surface (see, e.g., Reference 52), the DNA strand translocates through the nanopore in discrete steps (see, e.g., Reference 50), with the translocation probability being an exponential function of the transmembrane bias (see, e.g., References 50,53). Constrained by the time scale of the all-atom MD methods, a transmembrane bias of 10 V was chosen for these exploratory simulations, which enabled observation of multiple back-and forth motion of the DNA strand through the nanopores while preserving the stepwise character of the translocation process (see, e.g., FIG. 7—panel (b)). FIG. 15 illustrates the simulation trajectory. Repeating the simulations at a higher (20 V) and a lower (5 V) magnitude of the transmembrane potential, see, e.g., FIG. 11, confirmed the expected dependence of the translocation speed on the bias, see, e.g., FIG. 12. Thus, lowering the magnitude of the bias differential should enable flossing ssDNA at arbitrary low speeds, which would be highly advantageous for accurate recognition of the DNA nucleotides.

Flossing of the DNA molecule through two hBN nanopores repeatedly placed DNA nucleotides in statistically similar conformations. To demonstrate the utility of such repeat placement, extracted was a set of DNA conformations that featured the same nucleotide triplet (ATC, CAT, or TCA) in the nanopore constriction. Next the steric exclusion model (see, e.g., Reference 51) was used to compute the relative residual current for each DNA conformation and obtain the histogram of blockade currents for each nucleotide triplet, see, e.g., FIG. 7—panel (c). The resulting distributions exhibit considerable overlap, which is partially attributed to the extreme simulation time scale that may have precluded ssDNA nucleotides from finding an equilibrium low-energy conformation between consecutive translocation steps. Taking this worst-case scenario distribution as input, the probability can be assessed of correctly identifying the nucleotide triplets from the ionic current alone when they are subject to repeat nanopore ionic current measurement, see, e.g., FIG. 7—panel (d). With the single-read identification probability being slightly better than random, the identification fidelity increases to over 90% after moving DNA back and forth tens of times.

Close examination of the 10 V simulation trajectory, see, e.g., FIG. 7—panel (b), suggests that the stepwise displacement of ssDNA through the two nanopores is correlated. Such correlated motion was examined quantitatively by plotting the time at which each of the translocation steps occurred in each nanopore in the 5 V trajectory, see, e.g., FIG. 13. The individual translocation events through individual nanopores are found to occur within ~1 ns from one another, with only 3 uncorrelated events from 33 total stepwise displacements. Such highly correlated motion enables, in principle, accurate characterization of DNA homopolymer sequences, which is a long-standing problem for nanopore sequencing. In such a correlated motion scenario, the number of nucleotides in the homopolymer fragment passing through one nanopore could be discerned (according to an embodiment) by counting the number of nucleotides from a heterogeneous-sequence fragment of the same molecule passing through the other nanopore.

Reference will now be made to certain Conclusions according to an embodiment. In summary, described herein has been a nanofluidic double-nanopore system that has the potential to considerably increase the fidelity of DNA and RNA sequencing. Upon high-fidelity loading of a single DNA or RNA molecule into two pores, the sequence of the molecule can be read off as often as desired by flossing, yielding infinite-depth sequencing at the level of an individual molecule. This approach can lead to successful characterization of native, unamplified DNA molecules with rare epigenetic modifications and/or native, low in abundance RNA molecules that frequently carry biologically significant modifications that are normally lost in ensemble averaging. Finally, it is believed that a double-nanopore approach (according to an embodiment) can, at last, realistically provide a way to use solid-state nanopores as a superior and scalable technique for high-throughput, direct, and long-read nanopore sequencing of individual DNA and RNA molecules.

Practical implementation of infinite depth sequencing can include one or more of the following: One is device fabrication, which, in addition to sculpturing the delivery channels and the reader nanopores, can (in various embodiments) incorporate surface coating to prevent DNA sticking to the device surfaces (see, e.g., Reference 54). Another is developing approaches to handle biomedically relevant fragments of ssDNA and ssRNA molecules, which could involve hybridization to dsDNA handles. It is also noted that while a dual reader double-nanopore system can provide bumper-to-bumper DNA or RNA sequencing, it should also be possible to use a nanofluidic double-nanopore setup (according to an embodiment) with a single reading nanopore, where the latter could either be a nanopore in a 2D material or a biological nanopore incorporated in a lipid bilayer membrane (see, e.g., Reference 55).

As described herein, nanopore sequencing of nucleic acids has a history of innovations that eventually made commercial nanopore sequencing possible. Nevertheless, the conventional nanopore sequencing technology typically leaves much room for improvement, especially with respect to accuracy of raw reads and detection of nucleotide modifications. Double-nanopore sequencing, according to various embodiments described herein, can provide an approach (where a DNA molecule is pulled back and forth by a tug-of-war of two nanopores) that could potentially improve single-molecule read accuracy and modification detection by offering multiple reads of the same DNA fragment.

As described herein, one principal difficulty in realizing such a double-nanopore sequencing technology is threading single-stranded DNA through both nanopores. Described and demonstrated herein through simulations is a nanofluidic system for loading and threading DNA strands through a double-nanopore setup with nearly 100% fidelity. The high-efficiency loading can be realized by using hourglass-shaped side channels that not only deliver the molecules to the nanopore but also retain molecules that missed the nanopore at the first passage to attempt the nanopore capture again. The second nanopore capture can be facilitated by an orthogonal microfluidic flow that unravels the molecule captured by the first nanopore and delivers it to the capture volume of the second nanopore.

Demonstrated herein is the utility of a double-nanopore system (according to an embodiment) for DNA sequencing by simulating repeat back-and-forth motion (flossing) of a DNA strand through the double-nanopore system. It is shown that repeat exposure of the same DNA fragments to the nanopore sensing volume (according to an embodiment) considerably increases accuracy of the nucleotide sequence determination and that correlated displacement of ssDNA through the two nanopores can facilitate recognition of homopolymer fragments.

Reference will now be made to certain Methods according to an embodiment. More particularly, COMSOL software (COMSOL Multiphysics 5.3a) was used to obtain the distribution of the electrostatic potential and the fluid flow profiles. All simulations of ssDNA capture by the double-nanopore system were performed using the Atomic Resolution Brownian Dynamics (ARBD) package (see, e.g., Reference 56). The all-atom MD method (see, e.g., Reference 57) was combined with a steric exclusion model (SEM) (see, e.g., Reference 51) to simulate infinite-depth sequencing of an ssDNA molecule.

Still referring to certain Methods according to an embodiment, reference will now be made to Continuum Modeling of Electrostatics and Solvent Flow in a Double-Nanopore System according to an embodiment. The COMSOL software package was used to generate continuum solutions to the electrostatics and hydrostatics problems on the computational domain subject to boundary conditions. The computational domain was a 330×190×400 nm³ rectangle (see, e.g., FIG. 1E). It contained two identical delivery channels each connected through a nanopore to a common flow chamber. Each delivery channel had a rectangular cross section of 80×160 nm² at each end that linearly funneled down over a distance of 80 nm to a constriction, also 80 nm long, where the cross section was 25×50 nm². In the center of the constriction was an entrance to a cylindrical nanopore (10 nm in diameter and 10 nm in height), which extended from the delivery channel to the flow chamber. The two nanopores were separated by 170 nm. The walls between the two delivery channels were 10 nm thick; however this choice was made solely to keep the simulation volume small and is not critical for any of the results. The material properties of the interior of the system were set to those of water, i.e., 1000 kg/m³ density, 0.00089 Pa·s dynamic viscosity, and relative permittivity of 80.

The flow velocity was obtained using the Laminar Flow module, which solves the equations $$\rho(\vec{u}\cdot\vec{\nabla})\vec{u}=\vec{\nabla}\cdot(-\rho I+\mu(\vec{\nabla}\vec{u}+(\vec{\nabla}\vec{u})^T))+\vec{F}\rho\vec{\nabla}\cdot\vec{u}=0$$

where $\rho$, $\vec{u}$, $\mu$, I and F are the fluid density, velocity, dynamic viscosity, identity matrix and the volume force exerted on the fluid, respectively.

All fluid-solid interfaces were given a no-slip boundary condition, whereas applied pressure was specified at the open boundaries at the inlets and outlets of the channels and the flow chamber. The distribution of the electrostatic potential was obtained using the Electrostatics module, which solves the equations $$\vec{\nabla}\cdot\vec{D}=\rho_v$$

$$\vec{E}=-\vec{\nabla}V$$

where $\vec{E}$, $\vec{D}$, $\rho_v$, and V are the electric field, electric displacement, charge density and electric potential, respectively.

The external potential was introduced into the calculation as a boundary condition for each fluid inlet and outlet. In this way, the boundary of each of the three electrolyte-filled channels could be set to a potential value of choice, generating a strong electric field in the nanopores that connected them. A two-step process was used to obtain the mesh upon which COMSOL solved the differential equations. First, a custom free tetrahedral mesh was created using a predefined "extremely coarse" element size everywhere in the computational domain except for the volumes occupied by the nanopores and the rectangular constrictions of the delivery channels, where the size parameter was set to "extremely fine". Additionally, the maximum element size was set to 0.8 nm in the nanopore volume. The resulting mesh was used to find the initial solution to the electrostatics and the fluid flow problems under the boundary conditions of the first nanopore capture. The solution was further refined using an adaptive mesh procedure with a maximum coarsening factor of 1 and an element growth rate of 2.5. The resulting mesh was then saved and used to solve all of the electrostatic and fluid flow problems for the coarse-grained simulations described herein.

Still referring to certain Methods according to an embodiment, reference will now be made to Coarse-Grained MD Simulations of ssDNA Capture and Threading according to an embodiment. All simulations were performed using a GPU-accelerated simulation engine, ARBD (see, e.g., Reference 56), a 1 ps simulation time step, and a two-bead-per-nucleotide model of ssDNA that was developed to reproduce the equilibrium conformation and the force-extension properties of an unstructured DNA strand (see, e.g., Reference 58). A Langevin integration scheme was used to maintain a constant temperature with damping coefficients of 42.25 and 41.37 Å²/ns for P and B beads, respectively. The coarse-grained MD simulation of ssDNA was coupled to the electrostatic potentials extracted from a continuum COMSOL model in the form of an external grid-based potential that was applied to the backbone beads of the DNA. Each backbone bead was assigned an effective charge of 0.25 e, where e is the charge of an electron, to account for charge screening in the nanopore systems (see, e.g., References 59-61). Additionally, a repulsive steric potential was applied, in the form of a 3D grid potential, to prevent the DNA from penetrating the solid boundaries of the system, as well as the fluid inlets and outlets. The steric potential was generated using the find boundaries routine of the image processing Python module, scikit-image (see, e.g., Reference 62), to identify a set of boundary layers (in steps matching the 1 nm resolution of the grid) from the binary geometry data exported from COMSOL. The values of the steric potential were zero in the fluid channels and increased with each boundary layer n as $kn^2$, where k=100 kcal/mol. Finally, ARBD was modified to include a description of hydrostatic forces exerted by the flow of solvent extracted from the COMSOL model, as $\lambda(\vec{u}-\vec{v})$, where $\vec{v}$ is the velocity of the particle, $\vec{u}$ is the velocity of the fluid, and $\lambda$ is the Langevin damping coefficient of the beads. Note that this approach neglects the impact of the DNA on the fluid velocity.

Prior to capture simulations, a 1000 nt DNA strand was equilibrated in a 160×80×80 $nm^3$ volume using a multiresolution simulation protocol (see, e.g., Reference 63). The dimensions of this volume were identical to those of the entry rectangular compartment of the first cross delivery channel (see, e.g., FIG. 1E—view (a)). The initial conformation of the molecule was a 34 nm long straight line extending from the center of the volume along the x axis. The system was first simulated for 66 μs using a 10 ps time step with a resolution of 100 nt/bead. Following that, the system was simulated for 500 ns using a 500 fs time step at 5 nt/bead resolution and then for another 500 ns simulations at 1 nt/bead resolution. One hundred DNA conformations were created in this manner and used to initiate 100 independent capture simulations.

Still referring to certain Methods according to an embodiment, reference will now be made to All-Atom MD Simulations of ssDNA Flossing according to an embodiment. The all-atom MD simulations were performed using NAMD2 (see, e.g., Reference 64), a 2 fs time step, periodic boundary conditions, and the particle mesh Ewald (PME) method to calculate the long-range electrostatics (see, e.g., Reference 65). A Nosé-Hoover Langevin piston (see, e.g., References 66,67) and Langevin thermostat (see, e.g., Reference 68) were used to maintain constant pressure and constant temperature in the system. The CHARMM36 force field parameters (see, e.g., Reference 69) described the bonded and nonbonded interactions among DNA, water, and ions. The parameters for hBN were taken from Hilder et al. (see, e.g., Reference 70). A 8-10-12 Å cutoff scheme was used to calculate van der Waals and short-range electrostatics forces. The vdW interactions between atoms of DNA, boron nitride, water, and ions were determined using the Lorentz-Berthelot mixing rules.

SETTLE (see, e.g., Reference 71) and RATTLE (see, e.g., Reference 72) algorithms were applied to constrain bonds to hydrogen atoms in water and other covalent bonds, respectively. The system's coordinates were saved every 4.8 ps. The analysis and postprocessing of the simulation trajectories were performed using VMD (see, e.g., Reference 73).

A six-layer, 16×7.8 $nm^2$ patch of hBN was created using the Nanotube Builder plugin of VMD. The distance between consecutive layers of the hBN membrane was set to 3.35 Å, whereas the distance between the boron and nitrogen atoms within each layer was 1.45 Å. Atoms were removed from the hBN membrane to create a nanopore of 1.5 nm diameter and the shape of the M1-NNN MspA constriction (see, e.g., Reference 9). Bonds within the hBN membrane were generated across the periodic boundaries using the Inorganic Builder plugin of VMD. A 28-nucleotide ssDNA strand of 5'-$(TAC)_9$T-3' sequence was created using the NAB module of AMBERTOOLs.(see, e.g., Reference 74). Two nanopore systems were created by threading the same ssDNA molecule through the nanopore in two different global orientations: 3'-end or 5'-end first. Each system was then solvated in a box of TIP3P (see, e.g., Reference 75) water. Potassium and chloride ions were added to 2 M concentration using the Autoionize plugin of VMD. Each final assembled system measured 16>7.8>8 $nm^3$ and contained approximately 92,000 atoms.

Following the assembly, the systems underwent 1200 steps of energy minimization using the conjugate gradient method to remove steric clashes. The systems were then equilibrated for 50 ns at a constant number of atoms, pressure (1 bar), and temperature (300 K), with harmonic restraints applied to the boron and nitride atoms. The restraints were applied relative to the initial coordinates of the atoms, and the spring constants were 1 kcal/(mol $Å^2$). During the equilibration, the water attained the expected density of 1 $g/cm^3$ while the DNA bases adhered to the hBN surface.

The production simulation of the double-nanopore system (according to an embodiment) was performed under the constant volume and temperature conditions using the multicopy algorithm of NAMD (see, e.g., Reference 76) and a custom tclForces script to exchange the forces on the DNA strands between the two simulations. The phosphorus atom at the 3'-end of the DNA in one system was connected to the oxygen atom of the 5'-end of the DNA in the other system using a harmonic spring potential, mimicking a configuration in which one continuous DNA extends through the flow chamber. The spring constant was chosen to be 1.43 kcal/(mol $Å^2$) to match the experimental stretch modulus of ssDNA (see, e.g., Reference 77). A voltage bias of specified magnitude was applied alternatively across the membrane of one or the other system to floss the DNA. The voltage bias was switched when the position of the reference atoms connected via the harmonic springs' potential approached the boundary of the simulation system.

In various embodiments, a time scale associated with switching (e.g., a time between switching a voltage differential to an on state from an off state, a time between switching a voltage differential to an off state from an on state, a time that it takes to adjust (or change) a voltage differential from one value to another value, a time between switching a pressure differential to an on state from an off state, a time between switching a pressure differential to an off state from an on state, a time that it takes to adjust (or change) a pressure differential from one value to another value) can be in a range (inclusive) of from about 1 μs ($1 \times 10^{-6}$ second) to about 100 ms ($100 \times 10^{-3}$ second).

In various embodiments, a pressure (e.g., a pressure differential, an absolute pressure) can be in a range (inclusive) of from substantially 0 atm (atmosphere) to about 5 atm (atmosphere).

Figure 19:
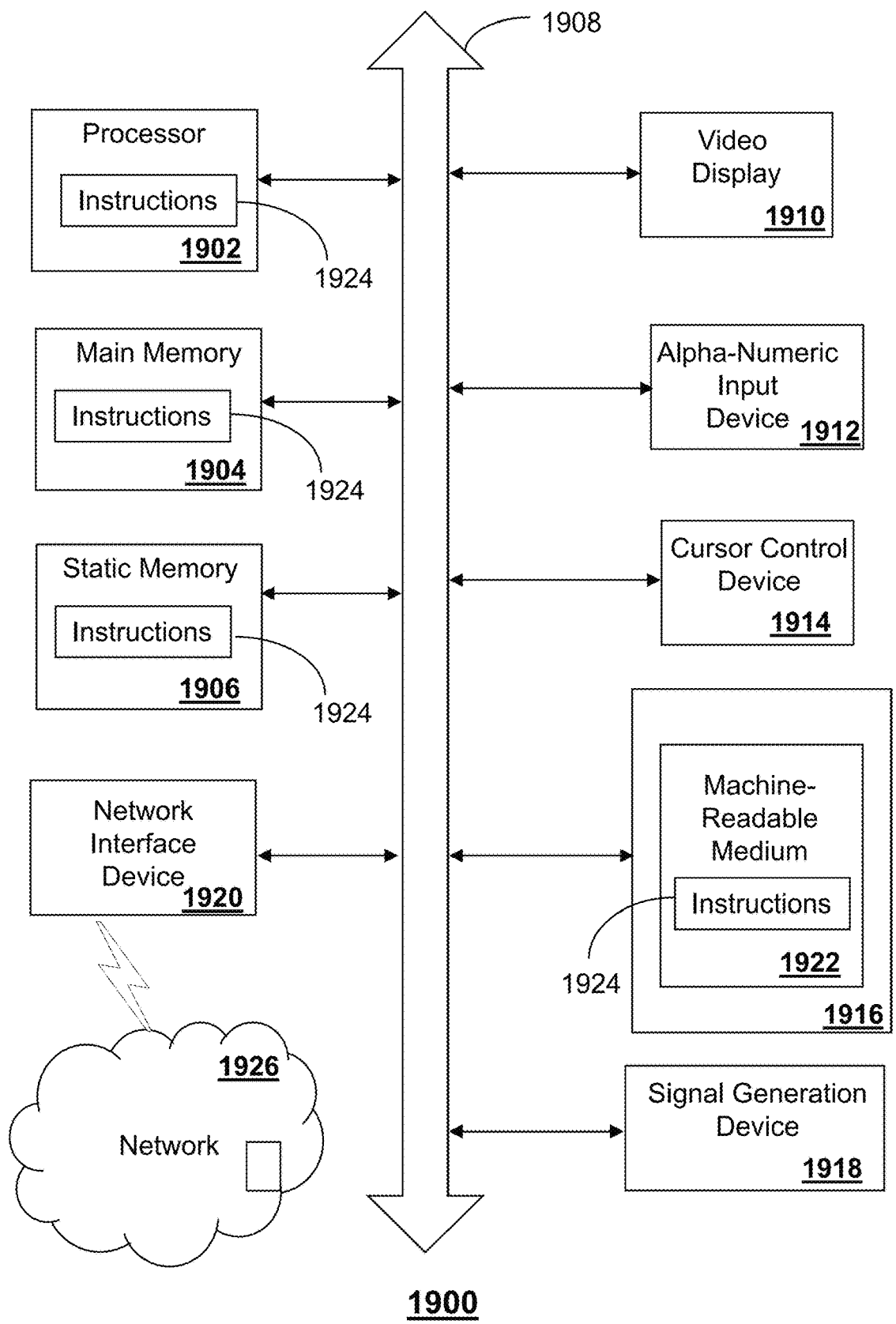
FIG. 19 depicts an illustrative diagrammatic representation of a machine in the form of a computer system within which a set of instructions, when executed, may cause the machine to perform any one or more of the methodologies disclosed herein.

Referring now to FIG. 19, this depicts an example diagrammatic representation of a machine in the form of a computer system 1900 within which a set of instructions, when executed, may cause the machine to perform any one or more of the methods discussed herein. In some embodiments, the machine may be connected (e.g., using a network) to other machines. In a networked deployment, the machine may operate in the capacity of a server or a client user machine in server-client user network environment, or as a peer machine in a peer-to-peer (or distributed) network environment.

The machine may comprise a server computer, a client user computer, a personal computer (PC), a tablet PC, a smart phone, a laptop computer, a desktop computer, a control system, a network router, switch or bridge, or any machine capable of executing a set of instructions (sequential or otherwise) that specify actions to be taken by that machine. It will be understood that a communication device of the subject disclosure includes broadly any electronic device that provides voice, video or data communication. Further, while a single machine is illustrated, the term "machine" shall also be taken to include any collection of machines that individually or jointly execute a set (or multiple sets) of instructions to perform any one or more of the methods discussed herein.

The computer system 1900 may include a processor 1902 (e.g., a central processing unit (CPU), a graphics processing unit (GPU, or both), a main memory 1904 and a static memory 1906, which communicate with each other via a bus 1908. The computer system 1900 may further include a video display unit 1910 (e.g., a liquid crystal display (LCD), a flat panel, or a solid-state display). The computer system 1900 may include an input device 1912 (e.g., a keyboard), a cursor control device 1914 (e.g., a mouse), a disk drive unit 1916, a signal generation device 1918 (e.g., a speaker or remote control) and a network interface device 1920.

The disk drive unit 1916 may include a tangible computer-readable storage medium 1922 on which is stored one or more sets of instructions (e.g., software 1924) embodying any one or more of the methods or functions described herein, including those methods illustrated above. The instructions 1924 may also reside, completely or at least partially, within the main memory 1904, the static memory 1906, and/or within the processor 1902 during execution thereof by the computer system 1900. The main memory 1904 and the processor 1902 also may constitute tangible computer-readable storage media.

Dedicated hardware implementations including, but not limited to, application specific integrated circuits, programmable logic arrays and other hardware devices can likewise be constructed to implement the methods described herein. Applications that may include the apparatus and systems of various embodiments broadly include a variety of electronic and computer systems. Some embodiments implement functions in two or more specific interconnected hardware modules or devices with related control and data signals communicated between and through the modules, or as portions of an application-specific integrated circuit. Thus, the example system is applicable to software, firmware, and hardware implementations.

In accordance with various embodiments of the subject disclosure, the methods described herein are intended for operation as software programs running on a computer processor. Furthermore, software implementations can include, but not be limited to, distributed processing or component/object distributed processing, parallel processing, or virtual machine processing can also be constructed to implement the methods described herein.

While the tangible computer-readable storage medium 1922 is shown in an example embodiment to be a single medium, the term "tangible computer-readable storage medium" should be taken to include a single medium or multiple media (e.g., a centralized or distributed database, and/or associated caches and servers) that store the one or more sets of instructions. The term "tangible computer-readable storage medium" shall also be taken to include any non-transitory medium that is capable of storing or encoding a set of instructions for execution by the machine and that cause the machine to perform any one or more of the methods of the subject disclosure.

The term "tangible computer-readable storage medium" shall accordingly be taken to include, but not be limited to: solid-state memories such as a memory card or other package that houses one or more read-only (non-volatile) memories, random access memories, or other re-writable (volatile) memories, a magneto-optical or optical medium such as a disk or tape, or other tangible media which can be used to store information. Accordingly, the disclosure is considered to include any one or more of a tangible computer-readable storage medium, as listed herein and including art-recognized equivalents and successor media, in which the software implementations herein are stored.

Although the present specification describes components and functions implemented in the embodiments with reference to particular standards and protocols, the disclosure is not limited to such standards and protocols. Each of the standards for Internet and other packet switched network transmission (e.g., TCP/IP, UDP/IP, HTML, HTTP) represent examples of the state of the art. Such standards are from time-to-time superseded by faster or more efficient equivalents having essentially the same functions. Wireless standards for device detection (e.g., RFID), short-range communications (e.g., Bluetooth, WiFi, Zigbee), and long-range communications (e.g., WiMAX, GSM, CDMA) are contemplated for use by computer system 1900.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

From the foregoing descriptions, it would be evident to an artisan with ordinary skill in the art that the aforementioned embodiments can be modified, reduced, or enhanced without departing from the scope and spirit of the claims described below. Other suitable modifications can be applied to the subject disclosure. Accordingly, the reader is directed to the claims for a fuller understanding of the breadth and scope of the subject disclosure.

The Abstract of the Disclosure is provided with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

REFERENCES (1) Bezrukov, S. M.; Vodyanoy, I.; Parsegian, V. A. Counting Polymers Moving through a Single Ion Channel. Nature 1994, 370, 279-281.

(2) Bayley, H.; Cremer, P. S. Stochastic Sensors Inspired by Biology. Nature 2001, 413, 226-230.

(3) Kasianowicz, J. J.; Brandin, E.; Branton, D.; Deamer, D. W. Characterization of Individual Polynucleotide Molecules Using a Membrane Channel. Proc. Natl. Acad. Sci. U.S.A. 1996, 93, 13770-13773.

(4) Wanunu, M. Nanopores: A Journey Towards DNA Sequencing. Phys. Life Rev. 2012, 9, 125-158.

(5) Howorka, S.; Siwy, Z. S. Nanopore Analytics: Sensing of Single Molecules. Chem. Soc. Rev. 2009, 38, 2360-2384.

(6) DeBlois, R. W.; Bean, C. P. Counting and Sizing of Submicron Particles by the Resistive Pulse Technique. Rev. Sci. Instrum. 1970, 41, 909-916.

(7) Luo, L.; German, S. R.; Lan, W.-J.; Holden, D. A.; Mega, T. L.; White, H. S. Resistive-Pulse Analysis of Nanoparticles. Annu. Rev. Anal. Chem. 2014, 7, 513-535.

(8) Akeson, M.; Branton, D.; Kasianowicz, J. J.; Brandin, E.; Deamer, D. W. Microsecond Time-Scale Discrimination among Polycytidylic Acid, Polyadenylic Acid, and Polyuridylic Acid as Homopolymers or as Segments Within Single RNA Molecules. Biophys. J. 1999, 77, 3227-3233.

(9) Manrao, E. A.; Derrington, I. M.; Laszlo, A. H.; Langford, K. W.; Hopper, M. K.; Gillgren, N.; Pavlenok, M.; Niederweis, M.; Gundlach, J. H. Reading DNA at Single-Nucleotide Resolution with a Mutant MspA Nanopore and Phi29 DNA Polymerase. Nat. Biotechnol. 2012, 30, 349-353.

(10) Timp, W.; Comer, J.; Aksimentiev, A. DNA Base-Calling from a Nanopore Using a Viterbi Algorithm. Biophys. J. 2012, 102, L37-L39.

(11) Laszlo, A. H.; Derrington, I. M.; Ross, B. C.; Brinkerhoff, H.; Adey, A.; Nova, I. C.; Craig, J. M.; Langford, K. W.; Samson, J. M.; Daza, R.; Doering, K.; Shendure, J.; Gundlach, J. H. Decoding Long Nanopore Sequencing Reads of Natural DNA. Nat. Biotechnol. 2014, 32, 829-833.

(12) Cherf, G. M.; Lieberman, K. R.; Rashid, H.; Lam, C. E.; Karplus, K.; Akeson, M. Automated Forward and Reverse Ratcheting of DNA in a Nanopore at 5-Å Precision. Nat. Biotechnol. 2012, 30, 344-348.

(13) Luan, B.; Stolovitzky, G.; Martyna, G. Slowing and Controlling the Translocation of DNA in a Solid-State Nanopore. Nanoscale 2012, 4, 1068-1077.

(14) Feng, J.; Liu, K.; Bulushev, R. D.; Khlybov, S.; Dumcenco, D.; Kis, A.; Radenovic, A. Identification of Single Nucleotides in MoS2 Nanopores. Nat. Nanotechnol. 2015, 10, 1070-1076.

(15) Belkin, M.; Chao, S.-H.; Jonsson, M. P.; Dekker, C.; Aksimentiev, A. Plasmonic Nanopores for Trapping, Controlling Displacement, and Sequencing of DNA. ACS Nano 2015, 9, 10598-10611.

(16) Yusko, E. C.; Bruhn, B. R.; Eggenberger, O. M.; Houghtaling, J.; Rollings, R. C.; Walsh, N. C.; Nandivada, S.; Pindrus, M.; Hall, A. R.; Sept, D.; Li, J.; Kalonia, D. S.; Mayer, M. Real-Time Shape Approximation and Fingerprinting of Single Proteins Using a Nanopore. Nat. Nanotechnol. 2017, 12, 360-367.

(17) Gershow, M.; Golovchenko, J. A. Recapturing and Trapping Single Molecules with a Solid-State Nanopore. Nat. Nanotechnol. 2007, 2, 775-779.

(18) Langecker, M.; Pedone, D.; Simmel, F. C.; Rant, U. Electrophoretic Time-of-Flight Measurements of Single DNA Molecules with Two Stacked Nanopores. Nano Lett. 2011, 11, 5002-5007.

(19) Liu, X.; Skanata, M. M.; Stein, D. Entropic Cages for Trapping DNA near a Nanopore. Nat. Commun. 2015, 6, 6222.

(20) Sampath, G. Amino Acid Discrimination in a Nanopore and the Feasibility of Sequencing Peptides with a Tandem Cell and Exopeptidase. RSC Adv. 2015, 5, 30694-30700.

(21) Pud, S.; Chao, S.-H.; Belkin, M.; Verschueren, D.; Huijben, T.; van Engelenburg, C.; Dekker, C.; Aksimentiev, A. Mechanical Trapping of DNA in a Double-Nanopore System. Nano Lett. 2016, 16, 8021-8028.

(22) Kasianowicz, J. J. Nanopores: Flossing with DNA. Nat. Mater. 2004, 3, 2355-356.

(23) Sánchez-Quesada, J.; Saghatelian, A.; Cheley, S.; Bayley, H.; Ghadiri, M. R. Single DNA Rotaxanes of a Transmembrane Pore Protein. Angew. Chem., Int. Ed. 2004, 43, 3063-3067.

(24) Cadinu, P.; Paulose Nadappuram, B.; Lee, D. J.; Sze, J. Y.; Campolo, G.; Zhang, Y.; Shevchuk, A.; Ladame, S.; Albrecht, T.; Korchev, Y.; Ivanov, A. P.; Edel, J. B. Single Molecule Trapping and Sensing Using Dual Nanopores Separated by a Zeptoliter Nanobridge. Nano Lett. 2017, 17, 6376-6384.

(25) Liu, X.; Zimny, P.; Zhang, Y.; Rana, A.; Nagel, R.; Reisner, W.; Dunbar, W. Flossing DNA in a Dual Nanopore Device. Small 2020, 16, 1613-6810.

(26) Yeh, J.-W.; Taloni, A.; Chen, Y.-L.; Chou, C.-F. Entropy-Driven Single Molecule Tug-of-War of DNA at Micro-Nanofluidic Interfaces. Nano Lett. 2012, 12, 1597-1602.

(27) Cadinu, P.; Campolo, G.; Pud, S.; Yang, W.; Edel, J. B.; Dekker, C.; Ivanov, A. P. Double Barrel Nanopores as a New Tool for Controlling Single-Molecule Transport. Nano Lett. 2018, 18, 2738-2745.

(28) Zhang, Y. N.; Liu, X.; Zhao, Y. A.; Yu, J. K.; Reisner, W.; Dunbar, W. B. Single Molecule DNA Resensing Using a Two-Pore Device. Small 2018, 14, 1801890.

(29) Liu, X.; Zhang, Y.; Nagel, R.; Reisner, W.; Dunbar, W. B. Controlling DNA Tug-of-War in a Dual Nanopore Device. Small 2019, 15, 1901704.

(30) Wanunu, M.; Sutin, J.; B, B. M.; Chow, A.; Meller, A. DNA Translocation Governed by Interactions with Solid-State Nanopores. Biophys. J. 2008, 95, 4716-4725.

(31) Freedman, K. J.; Otto, L. M.; Ivanov, A. P.; Batik, A.; Oh, S.-H.; Edel, J. B. Nanopore Sensing at Ultra-Low Concentrations Using Single-Molecule Dielectrophoretic Trapping. Nat. Commun. 2016, 7, 10217.

(32) Tian, K.; Decker, K.; Aksimentiev, A.; Gu, L.-Q. Interference-Free Detection of Genetic Biomarkers Using Synthetic Dipole-Facilitated Nanopore Dielectrophoresis. ACS Nano 2017, 11, 1204-1213.

(33) Brown, C. G.; Clarke, J. Nanopore Development at Oxford Nanopore. Nat. Biotechnol. 2016, 34, 810-811.

(34) Rahong, S.; Yasui, T.; Yanagida, T.; Nagashima, K.; Kanai, M.; Meng, G.; He, Y.; Zhuge, F.; Kaji, N.; Kawai, T.; Baba, Y. Three dimensional Nanowire Structures for Ultra-Fast Separation of DNA, Protein and RNA Molecules. Sci. Rep. 2015, 5, 10584.

(35) Briggs, K.; Madejski, G.; Magill, M.; Kastritis, K.; de Haan, H. W.; McGrath, J. L.; Tabard-Cossa, V. DNA Translocations through Nanopores under Nanoscale Preconfinement. Nano Lett. 2018, 18, 660-668.

(36) Ivanov, A. P.; Actis, P.; Jönsson, P.; Klenerman, D.; Korchev, Y.; Edel, J. B. On-Demand Delivery of Single DNA Molecules Using Nanopipets. ACS Nano 2015, 9, 3587-3595.

(37) Rahman, M.; Stott, M. A.; Harrington, M.; Li, Y.; Sampad, M. J. N.; Lancaster, L.; Yuzvinsky, T. D.; Noller, H. F.; Hawkins, A. R.; Schmidt, H. On Demand Delivery and Analysis of Single Molecules on a Programmable Nanopore-Optofluidic Device. Nat. Commun. 2019, 10, 3712.

(38) Sohi, A. N.; Beamish, E.; Tabard-Cossa, V.; Godin, M. DNA Capture by Nanopore Sensors under Flow. Anal. Chem. 2020, 92, 8108-8116.

(39) Zhou, J.; Wang, Y.; Menard, L. D.; Panyukov, S.; Rubinstein, M.; Ramsey, J. M. Enhanced Nanochannel Translocation and Localization of Genomic DNA Molecules Using Three-Dimensional Nanofunnels. Nat. Commun. 2017, 8, 807.

(40) Lu, B.; Hoogerheide, D. P.; Zhao, Q.; Zhang, H.; Tang, Z.; Yu, D.; Golovchenko, J. A. Pressure-Controlled Motion of Single Polymers through Solid-State Nanopores. Nano Lett. 2013, 13, 3048-3052.

(41) Mihovilovic, M.; Hagerty, N.; Stein, D. Statistics of DNA Capture by a Solid-State Nanopore. Phys. Rev. Lett. 2013, 110, 028102.

(42) Muthukumar, M. Polymer Translocation through a Hole. J. Chem. Phys. 1999, 111, 10371-10374.

(43) Li, J.; Stein, D.; McMullan, C.; Branton, D.; Aziz, M. J.; Golovchenko, J. A. Ion-Beam Sculpting at Nanometre Length Scales. Nature 2001, 412, 166-169.

(44) Storm, A. J.; Chen, J. H.; Ling, X. S.; Zandbergen, H. W.; Dekker, C. Fabrication of Solid-State Nanopore with Single-Nanometre Precision. Nat. Mater. 2003, 2, 537-540.

(45) Heng, J. B.; Ho, C.; Kim, T.; Timp, R.; Aksimentiev, A.; Grinkova, Y. V.; Sligar, S.; Schulten, K.; Timp, G. Sizing DNA Using a Nanometer-Diameter Pore. Biophys. J. 2004, 87, 2905-2911.

(46) Deamer, D.; Akeson, M.; Branton, D. Three Decades of Nanopore Sequencing. Nat. Biotechnol. 2016, 34, 518-524.

(47) Kasianowicz, J. J.; Bezrukov, S. M. On 'Three Decades of Nanopore Sequencing'. Nat. Biotechnol. 2016, 34, 481.

(48) Shekar, S.; Niedzwiecki, D. J.; Chien, C.-C.; Ong, P.; Fleischer, D. A.; Lin, J.; Rosenstein, J. K.; Drndic, M.; Shepard, K. L. Measurement of DNA Translocation Dynamics in a Solid-State Nanopore at 100 ns Temporal Resolution. Nano Lett. 2016, 16, 4483-4489.

(49) Venta, K.; Shemer, G.; Puster, M.; Rodriguez-Manzo, J. A.; Balan, A.; Rosenstein, J. K.; Shepard, K.; Drndic, M. Differentiation of Short, Single-Stranded DNA Homopolymers in Solid-State Nanopores. ACS Nano 2013, 7, 4629-4636.

(50) Wells, D. B.; Belkin, M.; Comer, J.; Aksimentiev, A. Assessing Graphene Nanopores for Sequencing DNA. Nano Lett. 2012, 12, 4117-4123.

(51) Wilson, J.; Sarthak, K.; Si, W.; Gao, L.; Aksimentiev, A. Rapid and Accurate Determination of Nanopore Ionic Current Using a Steric Exclusion Model. ACS Sens 2019, 4, 634-644.

(52) Lee, J.-H.; Choi, Y.-K.; Kim, H.-J.; Scheicher, R. H.; Cho, J.-H. Physisorption of DNA Nucleobases on h-BN and Graphene: vdWCorrected DFT Calculations. J. Phys. Chem. C 2013, 117, 13435-13441.

(53) Shankla, M.; Aksimentiev, A. Conformational Transitions and Stop-and-Go Nanopore Transport of Single-Stranded DNA on Charged Graphene. Nat. Commun. 2014, 5, 5171.

(54) Roy, R.; Hohng, S.; Ha, T. A Practical Guide to Single-Molecule FRET. Nat. Methods 2008, 5, 507-516.

(55) Gornall, J. L.; Mahendran, K. R.; Pambos, O. J.; Steinbock, L. J.; Otto, O.; Chimerel, C.; Winterhalter, M.; Keyser, U. F. Simple Reconstitution of Protein Pores in Nano Lipid Bilayers. Nano Lett. 2011, 11, 3334-3340.\

(56) Comer, J.; Aksimentiev, A. Predicting the DNA Sequence Dependence of Nanopore Ion Current Using Atomic-Resolution Brownian Dynamics. J. Phys. Chem. C 2012, 116, 3376-3393.

(57) Aksimentiev, A.; Heng, J. B.; Timp, G.; Schulten, K. Microscopic Kinetics of DNA Translocation through Synthetic Nanopores. Biophys. J. 2004, 87, 2086-2097.

(58) Maffeo, C.; Ngo, T. T. M.; Ha, T.; Aksimentiev, A. A Coarse-Grained Model of Unstructured Single-Stranded DNA Derived from Atomistic Simulation and Single-Molecule Experiment. J. Chem. Theory Comput. 2014, 10, 2891-2896.

(59) Keyser, U. F.; Koeleman, B. N.; van Dorp, S.; Krapf, D.; Smeets, R. M. M.; Lemay, S. G.; Dekker, N. H.; Dekker, C. Direct Force Measurements on DNA in a Solid-State Nanopore. Nat. Phys. 2006, 2, 473-477.

(60) Luan, B.; Aksimentiev, A. Electro-Osmotic Screening of the DNA Charge in a Nanopore. Phys. Rev. E 2008, 78, 021912.

(61) Hemmig, E.; Fitzgerald, C.; Maffeo, C.; Hecker, L.; Ochmann, S.; Aksimentiev, A.; Tinnefeld, P.; Keyser, U. Optical Voltage Sensing Using DNA Origami. Nano Lett. 2018, 18, 1962-1971.

(62) van der Walt, S.; Schönberger, J. L.; Nunez-Iglesias, J.; Boulogne, F.; Warner, J. D.; Yager, N.; Gouillart, E.; Yu, T. the scikitimage contributors, scikit-image: Image Processing in Python. PeerJ 2014, 2, No. e453.

(63) Maffeo, C.; Aksimentiev, A. MrDNA: A Multi-Resolution Model for Predicting the Structure and Dynamics of DNA Systems. Nucleic Acids Res. 2020, 48, 5135-5146.

(64) Phillips, J. C.; Hardy, D. J.; Maia, J. D. C.; Stone, J. E.; Ribeiro, J. V.; Bernardi, R. C.; Buch, R.; Fiorin, G.; Roux, J. H.; Aksimentiev, A.; Luthey-Schulten, Z.; Kale, L. V.; Schulten, K.; Chipot, C.; Tajkhorshid, E. Scalable Molecular Dynamics on CPU and GPU Architectures with NAMD. J. Chem. Phys. 2020, 153, 153.

(65) Batcho, P. F.; Case, D. A.; Schlick, T. Optimized Particle-Mesh Ewald/Multiple-Time Step Integration for Molecular Dynamics Simulations. J. Chem. Phys. 2001, 115, 4003-4018.

(66) Martyna, G. J.; Tobias, D. J.; Klein, M. L. Constant Pressure Molecular Dynamics Algorithms. J. Chem. Phys. 1994, 101, 4177-4189.

(67) Feller, S. E.; Zhang, Y.; Pastor, R. W.; Brooks, B. R. Constant Pressure Molecular Dynamics Simulation: The Langevin Piston Method. J. Chem. Phys. 1995, 103, 4613-4621.

(68) Brünger, A. T. X-PLOR, Version 3.1: a system for X-ray crystallography and NMR; Yale University Press, 1992.

(69) Hart, K.; Foloppe, N.; Baker, C. M.; Denning, E. J.; Nilsson, L.; MacKerell, A. D., Jr. Optimization of the CHARMM Additive Force Field for DNA: Improved Treatment of the BI/BII Conformational Equilibrium. J. Chem. Theory Comput. 2012, 8, 348-362.

(70) Hilder, T. A.; Yang, R.; Ganesh, V.; Gordon, D.; Bliznyuk, A.; Rendell, A. P.; Chung, S.-H. Validity of Current Force Fields for Simulations on Boron Nitride Nanotubes. Micro Nano Lett. 2010, 5, 150-156.

(71) Miyamoto, S.; Kollman, P. A. SETTLE: An Analytical Version of the SHAKE and RATTLE Algorithm for Rigid Water Molecules. J. Comput. Chem. 1992, 13, 952-962.

(72) Andersen, H. C. Rattle—A Velocity Version of the Shake Algorithm for Molecular-Dynamics Calculations. J. Comput. Phys. 1983, 52, 24-34.

(73) Humphrey, W.; Dalke, A.; Schulten, K. VMD: Visual Molecular Dynamics. J. Mol. Graphics 1996, 14, 33-38.

(74) Macke, T. J.; Case, D. A. Modeling Unusual Nucleic Acid Structures. Molecular Modeling of Nucleic Acids; American Chemical Society, 1998; Chapter 24, pp 379-393.

(75) Jorgensen, W. L.; Chandrasekhar, J.; Madura, J. D.; Impey, R. W.; Klein, M. L. Comparison of Simple Potential Functions for Simulating Liquid Water. J. Chem. Phys. 1983, 79, 926-935.

(76) Jiang, W.; Phillips, J. C.; Huang, L.; Fajer, M.; Meng, Y.; Gumbart, J. C.; Luo, Y.; Schulten, K.; Roux, B. Generalized Scalable Multiple Copy Algorithms for Molecular Dynamics Simulations in NAMD. Comput. Phys. Commun. 2014, 185, 908-916.

(77) Smith, S. B.; Cui, Y.; Bustamante, C. Overstretching B-DNA: The Elastic Response of Individual Double-Stranded and Single-Stranded DNA Molecules. Science 1996, 271, 795-799.

What is claimed is:

1. An apparatus comprising:
  a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, and wherein the second pore extends through the membrane from the first side of the membrane to the second side of the membrane;
  a first channel disposed on the first side of the membrane, wherein the first channel is along a first longitudinal axis;
  a second channel disposed on the first side of the membrane, wherein the second channel is along a second longitudinal axis, and wherein the first channel and the second channel are disposed side by side adjacent to each other;
  a third channel disposed on the second side of the membrane, wherein the third channel is along a third longitudinal axis, wherein the third channel is in first fluid communication with the first channel via the first pore, and wherein the third channel is in second fluid communication with the second channel via the second pore; and
  one or more sensors disposed at one or more locations to facilitate sequencing of a molecule that extends from the first channel, through the first pore across at least a portion of the third channel, and through the second pore into the second channel.

2. The apparatus of claim 1, further comprising:
  a first voltage source, the first voltage source being configured to apply a first voltage differential, in a first vicinity of the first pore, between the first channel and the third channel; and
  a second voltage source, the second voltage source being configured to apply a second voltage differential, in a second vicinity of the second pore, between the second channel and the third channel.

3. The apparatus of claim 2, wherein:
  the first voltage differential facilitates first movement of a first end of the molecule from the first channel, through the first pore, and into the third channel; and
  the second voltage differential facilitates second movement of the first end of the molecule from the third channel, through the second pore, and into the second channel.

4. The apparatus of claim 2, wherein the first voltage differential is controllable independently from the second voltage differential.

5. The apparatus of claim 2, wherein:
  the first voltage source facilitates first control of the first voltage differential independently of the second voltage differential; and
  the second voltage source facilitates second control of the second voltage differential independently of the first voltage differential.

6. The apparatus of claim 5, wherein the first control of the first voltage differential and the second control of the second voltage differential causes at least a portion of the molecule to be moved back and forth such that each of the one or more sensors is able to take multiple readings of the molecule.

7. The apparatus of claim 1, wherein the sequencing of the molecule comprises sequencing a portion of the molecule.

8. The apparatus of claim 1, wherein the molecule comprises a single stranded DNA (ssDNA).

9. The apparatus of claim 1, further comprising at least one mechanism configured to:
  apply a first pressure differential between a first end of the first channel and a second end of the first channel; and
  apply a second pressure differential between a first end of the second channel and a second end of the second channel.

10. The apparatus of claim 9, wherein:
  the first pressure differential facilitates movement of a first end of the molecule through the first channel, to a vicinity of the first pore; and
  the second pressure differential facilitates movement of the first end of the molecule through the second channel, away from a vicinity of the second pore.

11. The apparatus of claim 10, wherein:
  the at least one mechanism comprises at least one micro-pump;
  the at least one micro-pump comprises a first micro-pump and a second micro-pump;
  the first micro-pump applies the first pressure differential; and
  the second micro-pump applies the second pressure differential.

12. The apparatus of claim 11, wherein:
  the first micro-pump facilitates first control of the first pressure differential independently of the second pressure differential; and the second micro-pump facilitates second control of the second pressure differential independently of the first pressure differential.

13. The apparatus of claim 1, wherein:
the first longitudinal axis is substantially parallel to the second longitudinal axis; and
the third longitudinal axis is substantially perpendicular to the first longitudinal axis and to the second longitudinal axis.

14. The apparatus of claim 1, wherein:
the first channel has a first end, a second end, and a first middle section;
the first middle section has a smaller cross-sectional area than each of the first end and the second end;
the first middle section is located adjacent to the first pore;
the second channel has a third end, a fourth end, and a second middle section;
the second middle section has a smaller cross-sectional area than each of the third end and the fourth end; and
the second middle section is located adjacent to the second pore.

15. The apparatus of claim 1, further comprising a mechanism configured to apply a pressure differential between a first end of the third channel and a second end of the third channel, wherein the pressure differential facilitates movement of a first end of the molecule through the third channel, from a first vicinity of the first pore to a second vicinity of the second pore.

16. An apparatus comprising:
a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, and wherein the second pore extends through the membrane from the first side of the membrane to the second side of the membrane;
a first channel disposed on the first side of the membrane, wherein the first channel is along a first longitudinal axis;
a second channel disposed on the first side of the membrane, wherein the second channel is along a second longitudinal axis, and wherein the first channel and the second channel are disposed side by side adjacent to each other;
a third channel disposed on the second side of the membrane, wherein the third channel is along a third longitudinal axis, wherein the third channel is in first fluid communication with the first channel via the first pore, and wherein the third channel is in second fluid communication with the second channel via the second pore;
one or more sensors disposed at one or more locations to facilitate sequencing of a molecule that extends from the first channel, through the first pore across at least a portion of the third channel, and through the second pore into the second channel;
a first voltage source, the first voltage source being configured to apply a first voltage differential, in a first vicinity of the first pore, between the first channel and the third channel;
a second voltage source, the second voltage source being configured to apply a second voltage differential, in a second vicinity of the second pore, between the second channel and the third channel; and at least one mechanism configured to:
apply a first pressure differential between a first end of the first channel and a second end of the first channel; and
apply a second pressure differential between a first end of the second channel and a second end of the second channel.

17. The apparatus of claim 16, wherein:
the first voltage differential facilitates first movement of a first end of the molecule from the first channel, through the first pore, and into the third channel;
the second voltage differential facilitates second movement of the first end of the molecule from the third channel, through the second pore, and into the second channel; and
first control of the first voltage differential and second control of the second voltage differential causes at least a portion of the molecule to be moved back and forth.

18. The apparatus of claim 16, wherein the first voltage differential is controllable independently from the second voltage differential.

19. The apparatus of claim 16, wherein:
the first voltage source facilitates first control of the first voltage differential independently of the second voltage differential;
the second voltage source facilitates second control of the second voltage differential independently of the first voltage differential;
a first current meter measures a first current flow associated with the first voltage source, the measuring of the first current flow associated with the first voltage source facilitating a first determination of a type of nucleotide that is present on the molecule in the first vicinity of the first pore; and
a second current meter measures a second current flow associated with the second voltage source, the measuring of the second current flow associated with the second voltage source facilitating a second determination of a type of nucleotide that is present on the molecule in the second vicinity of the second pore.

20. An apparatus comprising:
a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, and wherein the second pore extends through the membrane from the first side of the membrane to the second side of the membrane;
a first channel disposed on the first side of the membrane, wherein the first channel is along a first longitudinal axis;
a second channel disposed on the first side of the membrane, wherein the second channel is along a second longitudinal axis, and wherein the first channel and the second channel are disposed side by side adjacent to each other;
a third channel disposed on the second side of the membrane, wherein the third channel is along a third longitudinal axis, wherein the third channel is in first fluid communication with the first channel via the first pore, and wherein the third channel is in second fluid communication with the second channel via the second pore;
one or more sensors disposed at one or more locations to facilitate sequencing of a molecule that extends from the first channel, through the first pore across at least a portion of the third channel, and through the second pore into the second channel; and at least one mechanism configured to:
- apply a first pressure differential between a first end of the first channel and a second end of the first channel; and
- apply a second pressure differential between a first end of the second channel and a second end of the second channel;

wherein the first longitudinal axis is substantially parallel to the second longitudinal axis; and wherein the third longitudinal axis is substantially perpendicular to the first longitudinal axis and to the second longitudinal axis.

21. An apparatus comprising:
a membrane, wherein the membrane has a first side and a second side, wherein the membrane has a first pore disposed therein, wherein the first pore extends through the membrane from the first side of the membrane to the second side of the membrane, wherein the membrane has a second pore disposed therein, and wherein the second pore extends through the membrane from the first side of the membrane to the second side of the membrane;

a first channel disposed on the first side of the membrane, wherein the first channel is along a first longitudinal axis;

a second channel disposed on the first side of the membrane, wherein the second channel is along a second longitudinal axis, and wherein the first channel and the second channel are disposed side by side adjacent to each other;

a third channel disposed on the second side of the membrane, wherein the third channel is along a third longitudinal axis, wherein the third channel is in first fluid communication with the first channel via the first pore, and wherein the third channel is in second fluid communication with the second channel via the second pore; and one or more sensors disposed at one or more locations to facilitate sequencing of a molecule that extends from the first channel, through the first pore across at least a portion of the third channel, and through the second pore into the second channel;

wherein the first longitudinal axis is substantially parallel to the second longitudinal axis;

wherein the third longitudinal axis is substantially perpendicular to the first longitudinal axis and to the second longitudinal axis;

wherein the first channel has a first end, a second end, and a first middle section;

wherein the first middle section has a smaller cross-sectional area than each of the first end and the second end;

wherein the first middle section is located adjacent to the first pore;

wherein the second channel has a third end, a fourth end, and a second middle section;

wherein the second middle section has a smaller cross-sectional area than each of the third end and the fourth end; and wherein the second middle section is located adjacent to the second pore.

22. The apparatus of claim 21, further comprising a mechanism configured to apply a pressure differential between a first end of the third channel and a second end of the third channel, wherein the pressure differential facilitates movement of a first end of the molecule through the third channel, from a first vicinity of the first pore to a second vicinity of the second pore.

* * * * *